United States Patent
Shah

(10) Patent No.: US 11,364,251 B2
(45) Date of Patent: *Jun. 21, 2022

(54) PHARMACEUTICAL FORMULATION

(71) Applicant: Semnur Pharmaceuticals, Inc., Palo Alto, CA (US)

(72) Inventor: Mahendra G. Shah, Mountain View, CA (US)

(73) Assignee: Semnur Pharmaceuticals, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/921,628

(22) Filed: Jul. 6, 2020

(65) Prior Publication Data

US 2021/0052605 A1    Feb. 25, 2021

Related U.S. Application Data

(63) Continuation of application No. 15/798,053, filed on Oct. 30, 2017, now Pat. No. 10,744,144, which is a continuation of application No. 14/162,625, filed on Jan. 23, 2014, now Pat. No. 9,833,460.

(60) Provisional application No. 61/776,617, filed on Mar. 11, 2013, provisional application No. 61/755,723, filed on Jan. 23, 2013.

(51) Int. Cl.
| | | |
|---|---|---|
| *A61K 31/573* | (2006.01) | |
| *A61K 31/661* | (2006.01) | |
| *A61K 31/58* | (2006.01) | |
| *A61K 9/00* | (2006.01) | |
| *A61K 47/36* | (2006.01) | |
| *A61K 45/06* | (2006.01) | |

(52) U.S. Cl.
CPC .......... *A61K 31/573* (2013.01); *A61K 9/0019* (2013.01); *A61K 31/58* (2013.01); *A61K 31/661* (2013.01); *A61K 45/06* (2013.01); *A61K 47/36* (2013.01)

(58) Field of Classification Search
CPC .... A61K 31/573; A61K 31/662; A61K 31/58; A61K 2300/00; A61K 9/0019; A61K 47/36; A61K 45/06

See application file for complete search history.

(56) References Cited

U.S. PATENT DOCUMENTS

| | | |
|---|---|---|
| 3,962,430 A | 6/1976 | O'Neill |
| 4,304,765 A | 12/1981 | Shell et al. |
| 5,106,615 A | 4/1992 | Dikstein |
| 6,251,876 B1 | 6/2001 | Bellini et al. |
| 6,747,090 B2 | 6/2004 | De Groot |
| 8,846,094 B2 | 9/2014 | Lyons et al. |
| 9,089,478 B2 | 7/2015 | Whitcup et al. |
| 9,833,460 B2 * | 12/2017 | Shah ................ A61K 47/36 |
| 10,117,938 B2 | 11/2018 | Shah |
| 10,500,284 B2 | 12/2019 | Shah |
| 10,744,144 B2 * | 8/2020 | Shah ................ A61P 29/00 |
| 11,020,485 B2 | 6/2021 | Shah |
| 2004/0006052 A1 | 1/2004 | Gudas et al. |
| 2005/0095235 A1 | 5/2005 | Austin et al. |
| 2005/0186229 A1 | 8/2005 | Clemente et al. |
| 2007/0020325 A1 | 1/2007 | Kuribayashi et al. |
| 2007/0099882 A1 | 5/2007 | Gurney et al. |
| 2007/0141160 A1 | 6/2007 | Brown et al. |
| 2007/0203095 A1 | 8/2007 | Sadozai et al. |
| 2009/0062720 A1 | 3/2009 | Anderson et al. |
| 2011/0281834 A1 | 11/2011 | Friden |
| 2013/0136780 A1 | 6/2013 | Tezel et al. |
| 2013/0142837 A1 | 6/2013 | Torrella et al. |
| 2018/0235980 A1 | 8/2018 | Shah |
| 2020/0197523 A1 | 6/2020 | Shah |

FOREIGN PATENT DOCUMENTS

| | | |
|---|---|---|
| CN | 1843333 A | 10/2006 |
| CN | 101918002 A | 12/2010 |
| EP | 0244178 A2 | 11/1987 |
| EP | 2067442 A1 | 6/2009 |
| GB | 1090492 A | 11/1967 |
| JP | 11-279065 A | 10/1999 |
| RU | 2459615 C1 | 8/2012 |
| WO | WO-1997/025025 A1 | 7/1997 |
| WO | WO-2008/157057 A2 | 12/2008 |
| WO | WO-2009/129148 A2 | 10/2009 |
| WO | WO-2009/129148 A3 | 10/2009 |
| WO | WO-2009/139924 A2 | 11/2009 |
| WO | WO-2009/139924 A3 | 11/2009 |
| WO | WO-2012/019009 A1 | 2/2012 |
| WO | WO-2013/096857 A1 | 6/2013 |

(Continued)

OTHER PUBLICATIONS

Barry, "Hyaluronic Acid Equivalent to Sham Injections in Patients with Knee DJD," American Family Physician 93(8):704(2016).
Database WPI, Week 200004, Thomson Scientific, London, GB;AN 2000-041984 & JP H11 279065 A (Shiseido Co Ltd) Oct. 12, 1999 (Oct. 12, 1999), 1 page.
Dollo, G et al., "Prolongation of Epidural Bupivacaine Effects with Hyaluronic Acid in Rabbits," Intl. J. Pharmaceutics, 272:109-119 (2004).
Ex Parte Quayle Office Action mailed on May 20, 2019, for U.S. Appl. No. 15/545,204, filed Jul. 20, 2017, 5 pages.
Fernandez-Palazzi, F. et al. (1997). "Intraarticular Dexamethasone in Advanced Chronic Synovitis in Hemophilia," Clinical Orthopaedics and Related Research 343:25-29.
Final Office Action dated Aug. 1, 2016, for U.S. Appl. No. 14/162,625, filed Jan. 23, 2014, 9 pages.

(Continued)

*Primary Examiner* — Ali Soroush
(74) *Attorney, Agent, or Firm* — Cooley LLP

(57) ABSTRACT

Disclosed are aqueous pharmaceutical compositions which provide sustained released delivery of corticosteroid compounds. The pharmaceutical composition comprises an insoluble corticosteroid; a soluble corticosteroid; and at least one viscosity enhancing agent. Also provided are methods for using the pharmaceutical compositions in an epidural injection, intra-articular injection, intra-lesional injection, or an intra-ocular injection.

20 Claims, 11 Drawing Sheets

(56) References Cited

FOREIGN PATENT DOCUMENTS

WO   WO-2014/116876 A1   7/2014
WO   WO-2016/118649 A1   7/2016

OTHER PUBLICATIONS

Gazelka, H.M. et al. (2012). "Determination of the Particulate Size and Aggregation of Clonidine and Corticosteroids for Epidural Steroid Injection," Pain Physician 15:87-93.

Grecomoro, et al., "Therapeutic synergism between hyaluronic acid and dexamethasone in the intra-articular treatment of osteoarthritis of the knee: a preliminary open study," Current Medical Research and Opinion 13(1):49-55 (1992).

International Preliminary Report on Patentability dated Jul. 25, 2017, by the International Searching Authority for Application No. PCT/US2016/014165, filed Jan. 20, 2016, 10 pages.

International Search Report and Written Opinion dated May 2, 2016, by the International Searching Authority for Application No. PCT/US2016/014165, filed Jan. 20, 2016, 14 pages.

International Search Report and Written Opinion dated Apr. 16, 2014, for PCT Patent Application No. PCT/US2014/012824, filed on Jan. 23, 2014, 19 pages.

Klingenberg, "Hyaluronic Acid—Creation of Slow-release Formulations for Osteoarthritis Treatments" Clinical & Medical Research International Pharmaceutical Industry 5(4):48-53 (2013).

Macmahon, P.J. et al. (2009). "Injectable corticosteroid and local anesthetic preparations: a review for radiologists," Radiology 252(3):647-661.

Mehta, D.P. et al. (2007). "Sodium hyaluronate of defined molecular size for treating osteoarthritis," Current Science 92(2):209-213.

Neustadt, D.H. (2006). "Intra-Articular Injections for Osteoarthritis of the Knee," Cleveland Clinic Journal of Medicine 73(10):897-911.

Non-Final Office Action issued by The United States Patent and Trademark Office for U.S. Appl. No. 15/545,204, dated Oct. 2, 2018, 9 pages.

Non-Final Office Action dated Jun. 15, 2018 for U.S. Appl. No. 15/798,053, filed Oct. 30, 2017, 6 pages.

Non-Final Office Action dated Feb. 2, 2016, for U.S. Appl. No. 14/162,625, filed Jan. 23, 2014, 7 pages.

Non-Final Office Action dated Mar. 9, 2017, for U.S. Appl. No. 14/162,625, filed Jan. 23, 2014, 9 pages.

Notice of Allowance issued by The United States Patent and Trademark Office for U.S. Appl. No. 15/907,057, dated Aug. 24, 2018, 8 pages.

Notice of Allowance dated Jul. 31, 2017, for U.S. Appl. No. 14/162,625, filed Jan. 23, 2014, 7 pages.

Notice of Allowance dated Dec. 26, 2018, for U.S. Appl. No. 15/798,053, filed Oct. 30, 2017, 8 pages.

Notice of Allowance dated Jul. 31, 2019, for U.S. Appl. No. 15/545,204, filed Jul. 20, 2017, 8 pages.

Non-Final Office Action issued by The United States Patent and Trademark Office for U.S. Appl. No. 15/907,057, dated May 10, 2018, 8 pages.

Paul, S. et al. (1999). "Pressure Measurements During Injection of Corticosteroids: In Vivo Studies," *Medical and Biological Engineering and Computing* 37:645-651.

Supplemental Notice of Allowability issued by The United States Patent and Trademark Office for U.S. Appl. No. 15/798,053, dated Jan. 14, 2019, 2 pages.

Notice of Allowance issued by The United States Patent and Trademark Office for U.S. Appl. No. 15/798,053, dated Apr. 3, 2020, 8 pages.

Non-Final Office Action dated Sep. 11, 2020 by The United States Patent and Trademark Office for U.S. Appl. No. 16/667,297, filed Oct. 29, 2019, 5 pages.

European Patent Office, Extended European Search Report for EP21173943.8, dated Nov. 11, 2021, 7 pages.

\* cited by examiner

FIG. 2

| Photomicrographs of Test Samples and Marketed Products ||
|---|---|
| 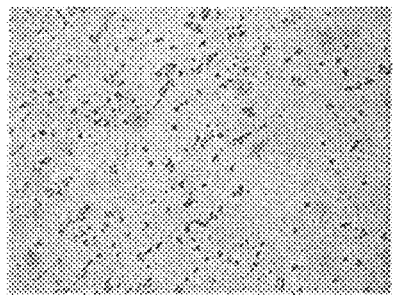<br>Test Sample 1<br>No Sodium Hyalorunidate<br>(N.B.#100.101.1722, p.12) | 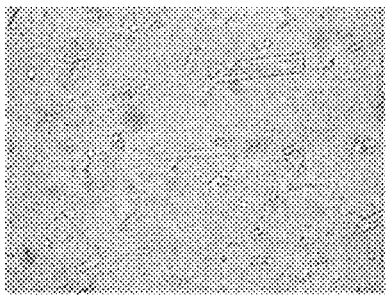<br>Celestone Soluspan<br>(Betamethasone Sodium Phosphate and Betamethasone Acetate, Injectable Suspension USP)<br>(Merck/ lot#043753) |
| 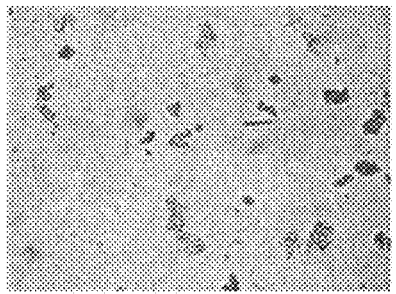<br>Test Sample 2<br>1.56M Sodium Hyalorunidate, 1.0% Solution<br>(N.B.#100.101.1722, p.12) | 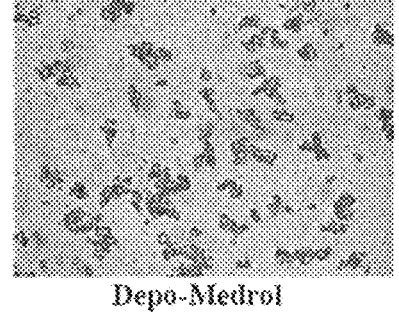<br>Depo-Medrol<br>(Methylprednisolone Acetate, Injectable Suspension USP)<br>(Pfizer/ lot#H18976) |
| 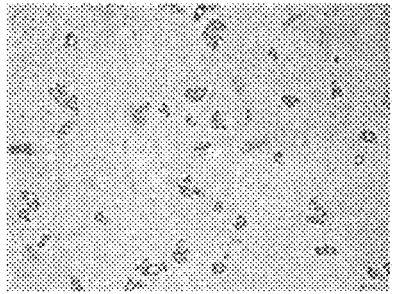<br>Test Sample 3<br>1.56M Sodium Hyalorunidate, 1.5% Solution<br>(N.B.#100.101.1722, p.12) | 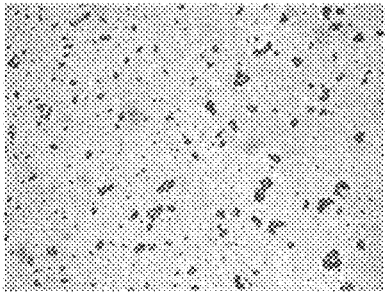<br>Kenalog-40<br>(Triamcinolone Acetonide, Injectable Suspension USP)<br>(Bristol-Myers Squibb/ lot#3F75331) |

PHARMACEUTICAL FORMULATION

CROSS-REFERENCE TO RELATED APPLICATIONS

This application is a continuation of U.S. application Ser. No. 15/798,053, filed Oct. 30, 2017, now U.S. Pat. No. 10,744,144, which is a continuation of U.S. application Ser. No. 14/162,625, filed Jan. 23, 2014, and titled "PHARMACEUTICAL FORMULATION", now U.S. Pat. No. 9,833,460, which claims benefit from U.S. Provisional Application No. 61/755,723, filed Jan. 23, 2013, and U.S. Provisional Application No. 61/776,617, filed Mar. 11, 2013, the disclosures of which are incorporated herein by reference in their entirety.

FIELD OF INVENTION

The present application relates to a pharmaceutical composition comprising both an insoluble form and a soluble form of a corticosteroid in water. The pharmaceutical composition is suitable for local administration such as epidural injection, intra-articular injection, and intra-lesional injection, and intra-ocular injection.

BACKGROUND OF THE INVENTION

In the spine, the epidural space (also known as "extradural space" or "peridural space") is the outermost part of the spinal canal. It is the space within the canal (formed by the surrounding vertebrae) lying outside the dura mater (which encloses the arachnoid mater, subarachnoid space, the cerebrospinal fluid, and the spinal cord). In humans, the epidural space contains lymphatics, spinal nerve roots, loose fatty tissue, small arteries, and a network of large, thin-walled blood vessels called the epidural venous plexus.

An epidural steroid injection is a minimally invasive procedure that can help relieve neck, arm, back, and leg pain in an individual caused by inflamed spinal nerves. For instance, an epidural steroid injection may be performed to relieve pain caused by spinal stenosis, spondylolysis, or disc herniation in an individual. Medicines are delivered to the spinal nerve through the epidural space, the area between the protective covering (dura) of the spinal cord and vertebrae. Corticosteroid injections can reduce inflammation and can be effective when delivered directly into the painful area of the individual.

Prednisolone is a corticosteroid drug with predominant glucocorticoid and low mineralocorticoid activity, making it useful for the treatment of a wide range of inflammatory and auto-immune conditions such as asthma, uveitis, pyoderma gangrenosum, rheumatoid arthritis, ulcerative colitis, temporal arteritis and Crohn's disease, Bell's palsy, multiple sclerosis, cluster headaches, vasculitis, acute lymphoblastic leukemia and autoimmune hepatitis, systemic lupus erythematosus, Kawasaki disease and dermatomyositis.

Methylprednisolone is typically used for its anti-inflammatory effects. The list of medical conditions for which methylprednisolone is prescribed is rather long, and is similar to other corticosteroids such as prednisolone. Common uses include arthritis therapy and short-term treatment of bronchial inflammation or acute bronchitis due to various respiratory diseases. It is used both in the treatment of acute periods and long-term management of autoimmune diseases, most notably systemic lupus erythematosus. It is also used as a treatment for multiple sclerosis.

Dexamethasone is a potent synthetic member of the glucocorticoid class of steroid drugs. It acts as an anti-inflammatory and immunosuppressant. Dexamethasone is used to treat many inflammatory and autoimmune conditions, such as rheumatoid arthritis and bronchospasm. Dexamethasone may also be used to treat idiopathic thrombocytopenic purpura, which is a decreased number of platelets due to an immune problem.

Triamcinolone acetonide is a synthetic corticosteroid with marked anti-inflammatory action. Kenalog®-10 Injection (triamcinolone acetonide injectable suspension, USP) is triamcinolone acetonide, in a sterile aqueous suspension suitable for intralesional and intra-articular injection, and not suitable for intravenous, intramuscular, intraocular, epidural, or intrathecal use. Each mL of the sterile aqueous suspension provides 10 mg triamcinolone acetonide, with sodium chloride for isotonicity, 0.9% (w/v) benzyl alcohol as preservative, 0.75% carboxymethylcellulose sodium, and 0.04% polysorbate 80; sodium hydroxide or hydrochloric acid may have been added to adjust pH between 5.0 and 7.5.

Betamethasone is a potent glucocorticoid steroid with anti-inflammatory and immunosuppressive properties. Betamethasone is used to treat the inflammation, swelling, and pain of arthritis. CELESTONE® SOLUSPAN® (betamethasone injectable suspension) Injectable Suspension is a sterile aqueous suspension containing 3 mg/mL betamethasone sodium phosphate, 3 mg/mL betamethasone acetate, 7.1 mg/mL dibasic sodium phosphate, 3.4 mg/mL monobasic sodium phosphate, 0.1 mg/mL edetate disodium, and 0.2 mg/mL benzalkonium chloride as preservative. The pH is between 6.8 and 7.2. CELESTONE® SOLUSPAN® is used for intra-articular administration and intralesional administration.

Existing pharmaceutical compositions may have immediate or short-term effects on alleviating pain. This may be sufficient for purposes of short-term administration such as to overcome an acute episode or exacerbation of pain. However, such formulations may require repeated administration, especially for sustained or chronic pain. In addition, for localized pain, epidural injections that result in the diffusion of the active ingredient outside of the target area may be undesirable and may increase the need for an overall higher dose to ensure that the target area is exposed to an effective dose. Furthermore, pharmaceutical compositions and methods of administration that contribute to unintended placement of the composition can lead to undesirable effects such as arachnoditis caused from an epidural injection.

There exists a need for an improved pharmaceutical composition that can provide a quick onset of action as well as a long lasting effect; have physical characteristics that facilitate injection into various parts of the body; and be shelf-stable. In particular, a stable, long-acting pharmaceutical composition suited for epidural, intra-articular, intra-lesional or intra-ocular injection is desirable.

SUMMARY OF THE INVENTION

In one aspect, the application discloses an aqueous pharmaceutical composition comprising an insoluble corticosteroid; a soluble corticosteroid; and at least one viscosity enhancing agent; having at least one of the features selected from the group consisting of: 1) the insoluble form of the corticosteroid has an average particle size of less than 10 µm; and 2) the pharmaceutical composition has a viscosity of between 1 kcP and 200 kcP.

In one embodiment, the application discloses an aqueous pharmaceutical composition, wherein the insoluble and soluble corticosteroid are selected from the group consisting of dexamethasone, methylprednisolone, prednisolone, triamcinolone acetonide, betamethasone, and salts and esters thereof. In another embodiment, the soluble corticosteroid is selected from the group consisting of dexamethasone sodium phosphate, methylprednisolone sodium succinate, prednisolone sodium succinate, triamcinolone acetonide phosphate ester, betamethasone sodium phosphate; and the insoluble corticosteroid is selected from the group consisting of dexamethasone acetate, methylprednisolone acetate, prednisolone acetate, triamcinolone acetonide acetate and betamethasone acetate. In yet another embodiment, the soluble corticosteroid is dexamethasone sodium phosphate and the insoluble corticosteroid is dexamethasone acetate.

In one embodiment, at least one viscosity enhancing agent is selected from the group consisting of sodium hyaluronate, hyaluronic acid, cross-linked hyaluronic acid, polyvinylpyrrolidone, hydroxypropyl methylcellulose, hydroxypropyl cellulose, hydroxethyl cellulose, and glycerol.

In another embodiment, the ratio of insoluble corticosteroid to soluble corticosteroid ranges from about 1:4 to 4:1. In some embodiments, the aqueous pharmaceutical composition comprises less than 2% w/v of the viscosity enhancing agent. In yet further embodiments, the aqueous pharmaceutical composition further comprises a preservative and/or an anesthetic.

In another aspect, the application provides a method for treating inflammation and/or pain in an individual in need thereof, comprising injecting into an individual an aqueous pharmaceutical composition disclosed herein. In one embodiment, the aqueous pharmaceutical composition is injected into the epidural space. In a further embodiment, less than 20 N of force is used to inject the aqueous pharmaceutical composition into the epidural space at a rate of about 0.5"/min. In yet another embodiment, the individual is injected with the aqueous pharmaceutical composition once every 4 to 24 weeks. In some embodiments, the insoluble form of the corticosteroid has an average particle size of less than 20 µm. In some embodiments, the formulation has a viscosity of between 1 kcP and 200 kcP. In some embodiments, the insoluble and soluble corticosteroid is selected from the group consisting of dexamethasone, methylprednisolone, prednisolone, and triamcinolone or salts and esters thereof. In further embodiments, the soluble form of the corticosteroid is selected from the group consisting of dexamethasone sodium phosphate, methylprednisolone sodium succinate, prednisolone sodium succinate, and triamcinolone acetonide phosphate ester; and the insoluble form of the corticosteroid is selected from the group consisting of dexamethasone acetate, methylprednisolone acetate, prednisolone acetate, and triamcinolone acetonide acetate. In yet other embodiments, the at least one viscosity enhancing agent is selected from the group consisting of sodium hyaluronoate, hyaluronic acid, cross-linked hyaluronic acid, polyvinylpyrrolidone, hydroxypropyl methylcellulose, hydroxypropyl cellulose, hydroxethyl cellulose, and glycerol. In certain embodiments, the ratio of insoluble corticosteroid to soluble corticosteroid ranges from about 1:4 to 4:1. In other embodiments, the aqueous pharmaceutical composition comprises less than 2% of the viscosity enhancing agent. In further embodiments, the aqueous pharmaceutical composition further comprises a preservative and/or an anesthetic.

In yet another aspect, the application provides a syringe comprising an aqueous pharmaceutical composition disclosed herein.

BRIEF DESCRIPTION OF THE DRAWINGS

FIG. 2 shows photomicrographs of test samples 1-3 and marketed products.

DETAILED DESCRIPTION OF THE INVENTION

Figure 1A:
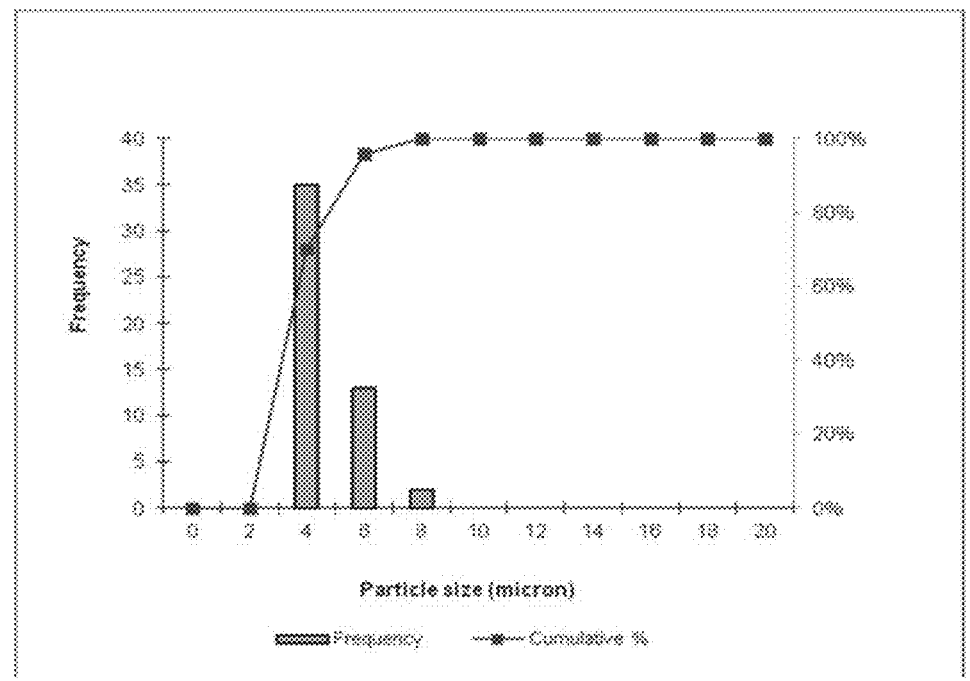
FIGS. 1A-1F shows particle size distribution of test samples 1 (1A), 2 (1B), and 3 (1C); and marketed samples 1 (1D), 2, (1E) and 3 (1F).
Figure 1B:
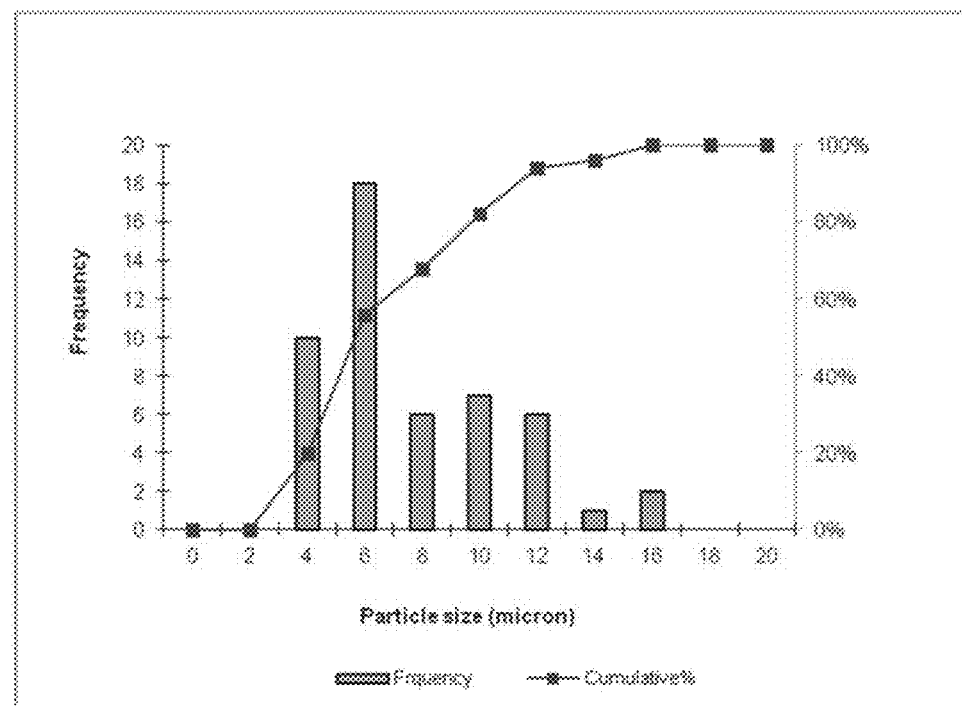
Figure 1C:
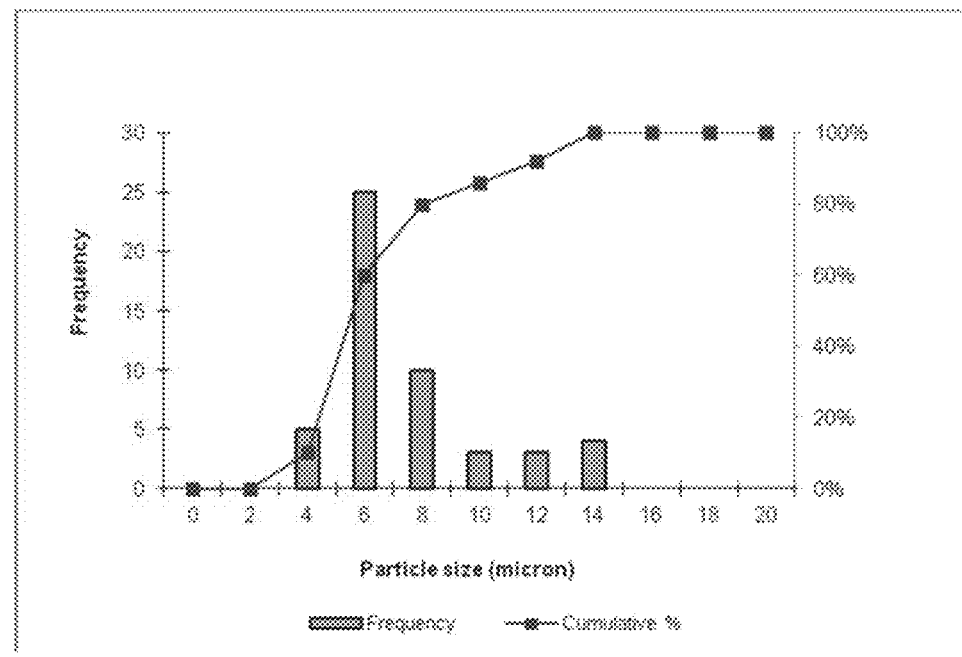
Figure 1D:
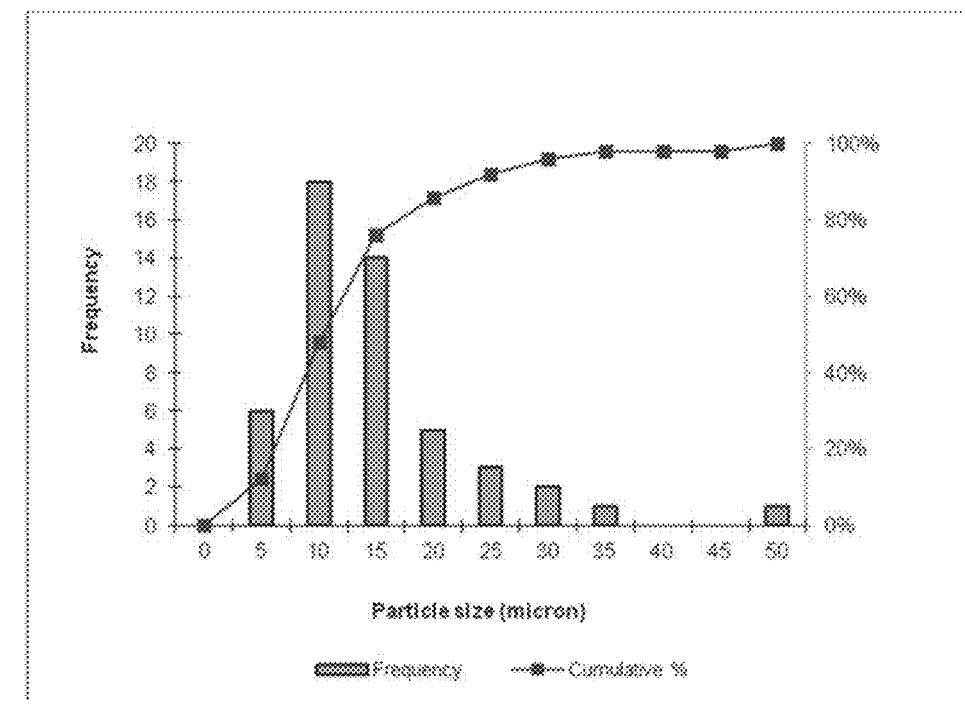
Figure 1E:
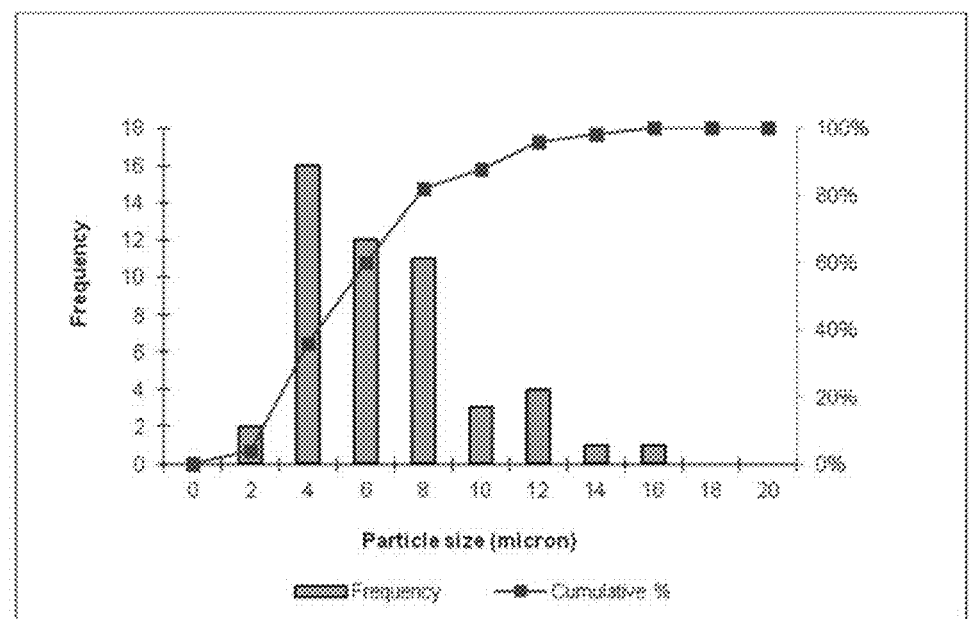
Figure 1F:
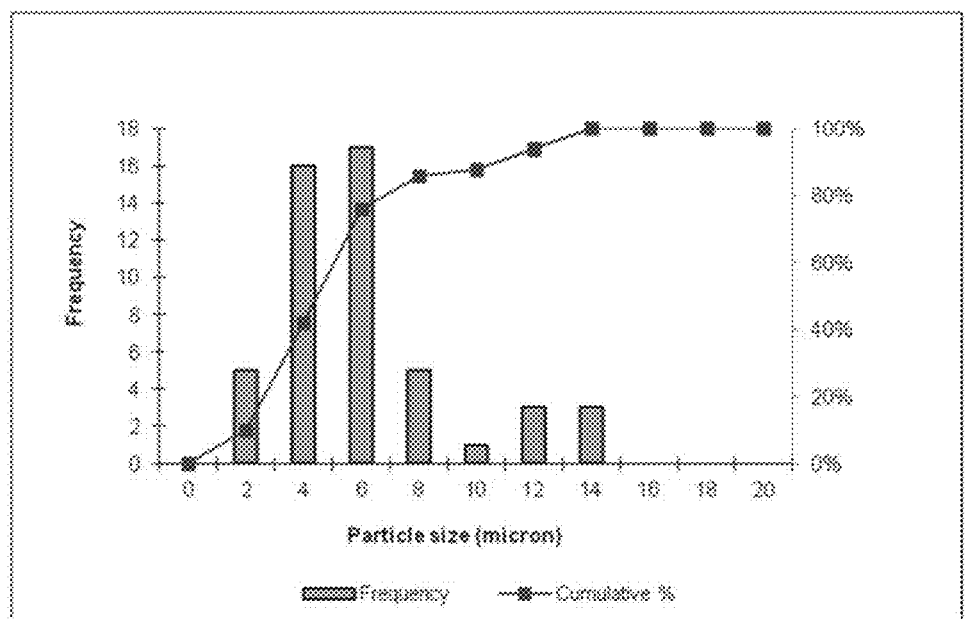

The present application is directed to a pharmaceutical composition comprising both an insoluble form and a soluble form of a corticosteroid in water. The pharmaceutical composition is suitable for local administration such as epidural injection, intra-articular injection, and intra-lesional injection, and intra-ocular injection. Suitable corticosteroids for the present application include methylprednisolone, dexamethasone, predinisolone, triamcinolone acetonide, and betamethasone; as well as salts or esters thereof.

The inventor has discovered the advantages of combining both an insoluble form and a soluble form of a corticosteroid in a pharmaceutical composition for a local injection. The local injection of a soluble form may provide a rapid onset but short duration of action when compared with less soluble preparations. A steroid in a soluble form provides quick action on a target site such as inflamed nerves and tissues, while a steroid in an insoluble form likely becomes available slowly for action while providing a longer lasting effect. The long lasting effect may allow a steroid to be injected periodically instead injected daily, which is difficult to do via epidural or intra-articular administration. The pharmaceutical composition of the present application may provide a quick onset of action and a long lasting effect.

Corticosteroids

Soluble form of the corticosteroid. Non-limiting examples of corticosteroids include dexamethasone, methylprednisolone, prednisolone, and triamcinolone acetonide, and salts or esters thereof. A soluble corticosteroid, as provided herein, provides an immediate or fast-acting effect after being administered to an individual. The soluble corticosteroid may possess a range of solubilities, however, it is soluble enough to be dissolved in the pharmaceutical formulation. The solubility of the corticosteroid is determined in part by its chemical form, such as salts or esters. Soluble forms of corticosteroids include salts thereof, such as sodium, phosphate, succinate, and combinations thereof.

Non-limiting examples of soluble corticosteroids include dexamethasone sodium phosphate, methylprednisolone sodium succinate, prednisolone sodium succinate, triamcinolone acetonide phosphate ester, and betamethasone sodium phosphate.

Insoluble form of the corticosteroid. An insoluble corticosteroid, as provided herein, provides a delayed or long-acting effect after being administered to an individual. As used herein, an "insoluble corticosteroid" may possess a range of solubilities, and in some embodiments, the insoluble corticosteroid exists as a particle in the pharmaceutical formulation. The insoluble corticosteroid is not totally insoluble, but dissolves over time to provide a source of the drug for the individual after the soluble corticosteroid is no longer available. It is understood that the "soluble" and "insoluble" terms as used herein is meant to describe the two forms of the corticosteroid in relative terms and is used to describe forms of the corticosteroids that provide an immediate and delayed effect, respectively, after administration to the individual. In some embodiments, one injection of the insoluble corticosteroid into an individual, provides a source of corticosteroid for at least about 4, about 6, about 8, about 10, about 12, about 14, about 16, about 18, about 20, about 22, or about 24 weeks. In some embodiments, the source of the corticosteroid provides an amount effective to reduce or inhibit inflammation and/or pain.

Non-limiting examples of the insoluble corticosteroid are dexamethasone, methylprednisolone, prednisolone, triamcinolone acetonide, salts and esters thereof. A specific example is an acetate ester of the corticosteroid. In some embodiments, non-limiting examples of the insoluble corticosteroid include dexamethasone acetate, methylprednisolone acetate, prednisolone acetate, triamcinolone acetonide acetate, and betamethasone acetate.

Particle size of the insoluble corticosteroid. The insoluble corticosteroid may exist as particles suspended and dispersed throughout the pharmaceutical composition. The particle size of the insoluble corticosteroid, in combination with other factors such as temperature, and composition viscosity, may influence the tendency of the particles to aggregate, settle, unevenly disperse throughout the pharmaceutical composition. Aggregation of insoluble corticosteroid particles may change the release profile of the drug.

In some embodiments, the particle size of the insoluble corticosteroid is less than 2 µm, 3 µm, 4 µm, 5 µm, 6 µm, 8 µm, 10 µm, or 20 µm. In some embodiments, the particle of the insoluble corticosteroid is between 2 µm and 20 µm, 2 µm and 10 µm, 2 µm and 5 µm, 2 µm and 3 µm, 3 µm and 20 µm, 3 µm and 10 µm, 3 µm and 5 µm, 3 µm and 4 µm, 4 µm and 20 µm, 4 µm and 10 µm, or 4 µm and 5 µm. In some embodiments, the insoluble particles is between 0.1 µm and 40 µm, 0.1 µm and 35 µm, 0.1 µm and 30 µm, 0.1 µm and 25 µm, 0.1 µm and 20 µm, 0.1 µm and 15 µm, 0.1 µm and 10 µm, 2.0 µm and 40 µm, 2.0 µm and 35 µm, 2.0 µm and 30 µm, 2.0 µm and 25 µm, 2 µm and 20 µm, 2.0 µm and 15 µm, or 2.0 µm and 10 µm. In some embodiments, the foregoing size range applies to most of the insoluble particles of the pharmaceutical composition. In some embodiments, the foregoing size range applies to at least 75%, 80%, 85%, 90%, 95%, 98% or 99% of the insoluble particles of the pharmaceutical composition.

In some embodiments, the insoluble corticosteroid particles are uniform in size, ±10%. In some embodiments, the insoluble corticosteroid particles are uniform in size, ±5%.

Ratio between soluble and insoluble forms. In general, the insoluble form and soluble form of the steroid are in a molar ratio of about 65-95 to 5-35. The molar ratio of insoluble to soluble corticosteroid may have a range of 2:1 to 19:1; 2:1 to 10:1; or 2:1 to 5:1. In one embodiment, the molar ratio of insoluble to soluble corticosteroid is 65:35, 75:25, 95:5, or 4:1.

In another embodiment, the weight ratio of insoluble to soluble corticosteroid may have a range of 2:1 to 19:1; 2:1 to 10:1; or 2:1 to 5:1. In one embodiment, the weight ratio of insoluble to soluble corticosteroid is 65:35, 75:25, 95:5, or 4:1.

In some of the foregoing embodiments, the soluble corticosteroid and the insoluble corticosteroid are selected from the group consisting of 1) dexamethasone sodium phosphate and dexamethasone acetate; 2) methylprednisolone sodium succinate and methylprednisolone acetate; 3) prednisolone sodium succinate and prednisolone acetate; 4) triamcinolone acetonide phosphate ester and triamcinolone acetonide acetate; and 5) betamethasone sodium phosphate and betamethasone acetate.

Additional Optional Components.

Viscosity enhancing agent. In one embodiment, a viscosity enhancing agent is included in the pharmaceutical composition. The viscosity enhancing agent provides an advantage that when the pharmaceutical composition is administered into a target site (e.g., the epidural space of an individual), the formulation stays longer in the target site due to a low degree of circulation of the viscous formulation in the target site. The viscosity enhancing agent may also promote the binding of the active drug to a target site and to enhance drug absorption and bioavailability locally.

The viscosity of the composition also contributes to the stability of the pharmaceutical composition. Higher viscosities may help reduce settling of insoluble particles and improves shelf-life. The viscosity of the composition is in large part influenced by the amount of the viscosity enhancing agent. Higher concentrations of the viscosity enhancing agent compared to lower concentrations results in a higher viscosity. Temperature also affects viscosity, with lower temperatures resulting in higher viscosities compared to higher temperatures of the same composition.

Suitable viscosity enhancing agent include sodium hyaluronate, hyaluronic acid, polyvinylpyrrolidone (PVP), cross-linked hyaluronic acid, hydroxypropyl methylcellulose, hydroxypropyl cellulose, hydroxylethyl cellulose, glycerol, or a mixture thereof. Preferred viscosity enhancing agents include sodium hyaluronate, polyvinylpyrrolidone (PVP), sodium hydroxypropyl cellulose, and carboxy methylcellulose. The present formulation does not include polyethylene glycol due to potential side effects.

The amount of the viscosity enhancing agent is based on the agent used, and is in general in an amount of about 0.05-30% (w/v). In some embodiments, the concentration of the viscosity enhancing agent is about 0.1% w/v, about 0.25% w/v, about 0.5% w/v, about 0.75% w/v, about 1.0% w/v, about 1.1% w/v, about 1.15% w/v, about 1.20% w/v, about 1.25% w/v, about 1.30% w/v, about 1.35% w/v, about 1.40% w/v, about 1.45% w/v, or about 1.5% w/v.

In some embodiments, the concentration of the viscosity enhancing agent is between 0.05% w/v and 1.5% w/v; 0.05% w/v and 0.5% w/v; 0.1% w/v and 3.0% w/v; 0.1% w/v and 1.5% w/v; 0.1% w/v and 1.0% w/v; 0.5% w/v and 1% w/v; 0.5% w/v and 2.5% w/v; 1.0% w/v and 3.0% w/v;

1.0% w/v and 1.5% w/v; 1.0% w/v and 1.25% w/v; 1.25% w/v and 1.5% w/v; or 1.5% w/v and 3.0% w/v.

In some embodiments, the molecular weight of the viscosity enhancing agent is between 500 kDa and 5.0 MDa; 500 kDa and 3.0 MDa; 500 kDa and 2.0 MDa; 500 kDa and 1.0 MDa; 500 kDa and 2.0 MDa; 1.0 MDa and 3.0 MDa; 1.0 MDa and 2.5 MDa; 1.0 MDa and 2.0 MDa; and 1.2 MDa and 1.8 MDa. In some embodiments, the molecular weights of sodium hyaluronate is about 711 kDa; about 880 kDa; about 1.56 MDa; about 1.8 MDa and about 2.65 MDa. In some of the embodiments, the molecular weight is the number average molecular weight, and in other embodiments the molecular weight is the weight average molecular weight. In some of the foregoing embodiments, the viscosity enhancing agent is sodium hyaluronate. In some embodiments, the viscosity enhancing agent is hyaluronic acid or a pharmaceutically acceptable salt of hyaluronate, such as sodium salt, phosphate salt or calcium salt.

In some embodiments, the viscosity of the pharmaceutical composition is about 300 kcP, about 250 kcP, about 200 kcP, about 150 kcP, about 140 kcP, about 130 kcP, about 120 kcP, about 110 kcP, about 100 kcP, about 90 kcP, about 80 kcP, about, 70 kcP, about 40 kcP, about, 30 kcP, about 25 kcP, about 20 kcP, about 10 kcP, about 5 kcP, or about 1 kcP.

In some embodiments, the viscosity of the composition is between 1 kcP and 300 kcP; 1 kcP and 100 kcP; 1 kcP and 50 kcP; 1 kcP and 10 kcP; 10 kcP and 50 kcP; 10 kcP and 100 kcP; 50 kcP and 100 kcP; 100 kcP and 300 kcP; 50 kcP and 200 kcP; 75 kcP and 180 kcP; 100 kcP and 150 kcP; 150 kcP and 200 kcP; 200 kcP and 250 kcP; 250 kcP and 300 kcP.

Particle size and viscosity combinations. In some compositions, the particle size is less than about 2 µm, about 3 µm, about 4 µm, about 5 µm, about 6 µm, about 8 µm, about 10 µm, or about 20 µm, and the viscosity of the formulation is between 1 kcP and 300 kcP. In some compositions, the particle size is less than about 2 µm, about 3 µm, about 4 µm, about 5 µm, about 6 µm, about 8 µm, about 10 µm, or about 20 µm and the viscosity of the formulation is between 1 kcP and 200 kcP. In some compositions, the particle size is less than about 2 µm, about 3 µm, about 4 µm, about 5 µm, about 6 µm, about 8 µm, about 10 µm, or about 20 µm and the viscosity of the formulation is between 1 kcP and 100 kcP. In some compositions, the particle size is less than about 2 µm, about 3 µm, about 4 µm, about 5 µm, about 6 µm, about 8 µm, about 10 µm, or about 20 µm and the viscosity of the formulation is between 100 kcP and 150 kcP. In some compositions, the particle size is less than about 5 µm, and the viscosity of the formulation is between 100 kcP and 150 kcP. In some compositions, the particle size is about 5 µm, and the viscosity of the formulation is between 100 kcP and 150 kcP. In some compositions, the particle size is about 5 µm, and the viscosity of the formulation is between 1 kcP and 50 kcP.

In some embodiments, the pharmaceutical composition is a gel. In alternative embodiments, the pharmaceutical composition is an aqueous solution.

Buffer. Suitable buffering agents for use with the pharmaceutical compositions disclosed herein include, but are not limited to, organic acid salts such as salts of citric acid, ascorbic acid, gluconic acid, carbonic acid, tartaric acid, succinic acid, acetic acid or phthalic acid; Tris, thomethamine hydrochloride, or phosphate buffer. In some embodiments, the buffer is physiologically compatible.

pH. The pH of the formulation may be inherently provided by the excipients present in the formulation; alternatively, a pH adjustment agent may be employed. A pH adjustment agent such as a buffer or a simple acid or base can be added to the pharmaceutical composition to maintain the pH to 6-8. For example, the amount of a pH adjusting agent is in general 0.1-10%. In some embodiments, the pH of the formulation is within physiological range.

Osmolality. The osmolality of the formulation is between 200 mOsm/kg and 350 mOsm/kg, 250 mOsm/kg and 300 mOsm/kg, 280 mOsm/kg and 290 mOsm/kg. In some embodiments, the osmolality of the formulation is within a physiological range. In some embodiments, the pharmaceutical composition is isotonic in a human.

Anesthetic. In one embodiment, the pharmaceutical composition further comprises an anesthetic agent such as lidocaine, bupivacaine, or benzocaine.

Surfactant. The present formulation preferably does not include a surfactant. However, in some embodiments, the pharmaceutical composition comprises one or more non-ionic surfactants. Inclusion of a surfactant increases the solubility and wettability of the drug particles. Suitable non-ionic surfactants include polysorbates (e.g., TWEEN®-80, TWEEN®-20), tyloxapol, polyoxyl castor oil, polaxamers, polyethylene glycol, caprylic triglyceride, polyoxyl stearates (e.g., oxyethylene monostearate), polyoxyethylated vegetable oils and glyceryl monostearate. A preferred non-ionic surfactant is a polysorbate such as TWEEN®-80. The amount of the non-ionic surfactant in the pharmaceutical composition, if present, is in general 0.001-10, or 0.01-1% (w/v) of the pharmaceutical composition.

Shelf life. The term "shelf life" refers to the amount of time the pharmaceutical composition may be stored without loss of potency and/or performance profile. In some embodiments, shelf life refers to the amount of time the pharmaceutical composition may be stored without a loss of more than 2,%, 5%, 8% or 10% of the potency and/or performance. The preservative-free pharmaceutical compositions provided herein are designed to have shelf life of at least 12, 24 or 36 months. In some embodiments, the pharmaceutical compositions have a shelf life of between 12 and 24 months. In some embodiments, the pharmaceutical composition is stored at room temperature and is shelf stable for at least 12, 24 or 36 months. In some embodiments, the pharmaceutical composition is stored below room temperature and has a shelf life of at least 12, 24, or 36 months.

Preservatives. In some embodiments, the pharmaceutical composition further comprises a preservative, such as an anti-microbial preservative, in order to increase the shelf-life of the pharmaceutical composition. Any preservative which does not adversely interact with the active drug or any of the excipients may be employed. For example, preservatives include ethanol, benzyl alcohol, benzalkonium chloride, benzethonium chloride, benzoic acid, bronopol, butyl-paraben, cetrimide, chlorhexidine. The amount of preservative may range, for example, from about 0.01-1%.

Exemplary Formulations

In one embodiment, the pharmaceutical composition comprises insoluble methylprednisolone acetate and soluble methylprednisolone sodium succinate in an aqueous solution such as water. For example, methylprednisolone acetate is in an amount of 65 to 95%, and methylprednisolone sodium succinate is in an amount of 5 to 35% of the methylprednisolone equivalent. The dose per injection of methylprednisolone is in the range of 20 to 120 mg/dose in 1 to 10 ml of a sterile solution such as water for injection or saline.

In one embodiment, the pharmaceutical composition comprises insoluble prednisolone acetate and soluble prednisolone sodium succinate in an aqueous solution such as water. For example, prednisolone acetate is in an amount of 65 to 95%, and prednisolone sodium succinate is in an amount of 5 to 35% of the prednisolone equivalent. The dose per injection for prednisolone is in the range of 20 to 120 mg/dose in 1 to 10 ml of a sterile solution such as water for injection or saline.

In one embodiment, the pharmaceutical composition comprises insoluble dexamethasone acetate and soluble dexamethasone sodium phosphate in an aqueous solution such as water. For example, dexamethasone acetate is in an amount of 65 to 95% and dexamethasone sodium phosphate is in an amount of 5 to 35% of the dexamethasone equivalent. The dose per injection of dexamethasone is in the range of 3 to 20 mg/dose in 1 to 10 ml of a sterile solution such as water for injection or saline.

Yet in another embodiment, the pharmaceutical composition comprises insoluble triamcinolone acetonide acetate and soluble triamcinolone acetonide phosphate ester in water. For example, triamcinolone acetonide acetate is an amount of 65 to 95% and triamcinolone acetonide phosphate is an amount of 5 to 35% of the triamcinolone equivalent. The dose per injection of triamcinolone is in the range of 20 mg to 120 mg/dose in 1 to 10 ml of a sterile solution such as water for injection or saline.

In one embodiment, the pharmaceutical composition comprises insoluble betamethasone acetate and soluble betamethasone sodium phosphate in an aqueous solution such as water. For example, betamethasone acetate is in a majority amount of 65 to 95% and betamethasone sodium phosphate is in a lesser amount of 5 to 35% of the betamethasone equivalent. The dose per injection of betamethasone is in the range of 3-50, or 3-20, or 6-50 mg/dose in 1 to 10 ml of a sterile solution such as water for injection or saline.

In one embodiment, the aqueous pharmaceutical composition comprises an insoluble corticosteroid; a soluble corticosteroid; and at least one viscosity enhancing agent; wherein the aqueous pharmaceutical composition comprises at least one of the features selected from the group consisting of: 1) the insoluble form of the corticosteroid has an average particle size of less than 10 µm; and 2) the pharmaceutical composition has a viscosity of between 1 kcP and 200 kcP. In some embodiments, the aqueous pharmaceutical composition is in a unit dose and has a volume of 1 mL, 2 mL, 3 mL, 4 mL, 5 mL, 6 mL, 7 mL, 8 mL, or 10 mL. In some embodiments, the viscosity enhancing agent concentration is between 0.05% w/v and 1.5% w/v; 0.05% w/v and 0.5% w/v; 0.1% w/v and 1.5% w/v; 0.1% w/v and 1.0% w/v; 0.5% w/v and 1% w/v; 0.5% w/v and 2.5% w/v; 1.0% w/v and 1.5% w/v; 1.0% w/v and 1.25% w/v; or 1.25% w/v and 1.5% w/v.

In further embodiments, the aqueous pharmaceutical composition comprises dexamethasone acetate; dexamethasone phosphate; and sodium hyaluronate; wherein the aqueous pharmaceutical composition comprises at least one of the features selected from the group consisting of: 1) the insoluble form of the corticosteroid has an average particle size of less than 10 µm; and 2) the pharmaceutical composition has a viscosity of between 1 kcP and 200 kcP. In some embodiments, the aqueous pharmaceutical composition is in a unit dose and has a volume of 1 mL, 2 mL, 3 mL, 4 mL, 5 mL, 6 mL, 7 mL, 8 mL, or 10 mL.

In further embodiments, the aqueous pharmaceutical composition comprises dexamethasone acetate; dexamethasone phosphate; and sodium hyaluronate; wherein the aqueous pharmaceutical composition comprises at least one of the features selected from the group consisting of: 1) dexamethasone acetate has an average particle size of less than 10 µm; and 2) the pharmaceutical composition has a viscosity of between 1 kcP and 200 kcP; wherein the sodium hyaluronate concentration is between 0.05% w/v and 1.5% w/v; 0.05% w/v and 0.5% w/v; 0.1% w/v and 1.5% w/v; 0.1% w/v and 1.0% w/v; 0.5% w/v and 1% w/v; 0.5% w/v and 2.5% w/v; 1.0% w/v and 1.5% w/v; 1.0% w/v and 1.25% w/v; or 1.25% w/v and 1.5% w/v. In some embodiments, the molecular weight of sodium hyaluronate is 500 kDa and 2.0 MDa. In other embodiments, the molecular weight of sodium hyaluronate is 1.2 MDa and 1.8 MDa. In some embodiments, the aqueous pharmaceutical composition is in a unit dose and has a volume of 1 mL, 2 mL, 3 mL, 4 mL, 5 mL, 6 mL, 7 mL, 8 mL, or 10 mL.

In further embodiments, the aqueous pharmaceutical composition comprises dexamethasone acetate; dexamethasone phosphate; and sodium hyaluronate; wherein the aqueous pharmaceutical composition comprises at least one of the features selected from the group consisting of: 1) dexamethasone acetate has an average particle size of about 5 µm; and 2) the pharmaceutical composition has a viscosity of between 1 kcP and 200 kcP; wherein the sodium hyaluronate concentration is between 0.05% w/v and 1.5% w/v; 0.05% w/v and 0.5% w/v; 0.1% w/v and 1.5% w/v; 0.1% w/v and 1.0% w/v; 0.5% w/v and 1% w/v; 0.5% w/v and 2.5% w/v; 1.0% w/v and 1.5% w/v; 1.0% w/v and 1.25% w/v; or 1.25% w/v and 1.5% w/v. In some embodiments, the molecular weight of sodium hyaluronate is 500 kDa and 2.0 MDa. In other embodiments, the molecular weight of sodium hyaluronate is 1.2 MDa and 1.8 MDa. In some embodiments, the aqueous pharmaceutical composition is in a unit dose and has a volume of 1 mL, 2 mL, 3 mL, 4 mL, 5 mL, 6 mL, 7 mL, 8 mL, or 10 mL.

Each of the exemplary formulations in Table 1 comprises a weight ratio of insoluble to soluble corticosteroid of 4:1 and a total corticosteroid weight of 5 mg, 10 mg, 15 mg, 20 mg, or 30 mg per dose. The size of the insoluble corticosteroid particles is about 5 µm. The molecular weight of the sodium hyaluronate is 1.56 MDa. The formulations further comprise a physiologically compatible buffer solution, such as 15 mM PBS solution. Each of the formulations are prepared in a 1 mL, 2 mL, 3 mL, 4 mL, 5 mL, 6 mL, 7 mL, 8 mL, and 10 mL unit doses.

TABLE 1

| # | Sodium hyaluronate, 1.56 MDa (% w/v) | dexamethasone acetate (mg) | dexamethasone sodium phosphate (mg) |
| --- | --- | --- | --- |
| 1 | 0.25 | 4 | 1 |
| 2 | 0.35 | 4 | 1 |
| 3 | 0.50 | 4 | 1 |
| 4 | 0.75 | 4 | 1 |
| 5 | 1.0 | 4 | 1 |
| 6 | 1.1 | 4 | 1 |
| 7 | 1.25 | 4 | 1 |
| 8 | 1.3 | 4 | 1 |
| 9 | 1.4 | 4 | 1 |
| 10 | 1.5 | 4 | 1 |
| 11 | 0.25 | 8 | 2 |
| 12 | 0.35 | 8 | 2 |
| 13 | 0.50 | 8 | 2 |
| 14 | 0.75 | 8 | 2 |
| 15 | 1.0 | 8 | 2 |
| 16 | 1.1 | 8 | 2 |
| 17 | 1.25 | 8 | 2 |
| 18 | 1.3 | 8 | 2 |
| 19 | 1.4 | 8 | 2 |
| 20 | 1.5 | 8 | 2 |
| 21 | 0.25 | 12 | 3 |
| 22 | 0.35 | 12 | 3 |

TABLE 1-continued

| # | Sodium hyaluronate, 1.56 MDa (% w/v) | dexamethasone acetate (mg) | dexamethasone sodium phosphate (mg) |
|---|---|---|---|
| 23 | 0.50 | 12 | 3 |
| 24 | 0.75 | 12 | 3 |
| 25 | 1.0 | 12 | 3 |
| 26 | 1.1 | 12 | 3 |
| 27 | 1.25 | 12 | 3 |
| 28 | 1.3 | 12 | 3 |
| 29 | 1.4 | 12 | 3 |
| 30 | 1.5 | 12 | 3 |
| 31 | 0.25 | 16 | 4 |
| 32 | 0.35 | 16 | 4 |
| 33 | 0.50 | 16 | 4 |
| 34 | 0.75 | 16 | 4 |
| 35 | 1.0 | 16 | 4 |
| 36 | 1.1 | 16 | 4 |
| 37 | 1.25 | 16 | 4 |
| 38 | 1.3 | 16 | 4 |
| 39 | 1.4 | 16 | 4 |
| 40 | 1.5 | 16 | 4 |
| 41 | 0.25 | 24 | 6 |
| 42 | 0.35 | 24 | 6 |
| 43 | 0.50 | 24 | 6 |
| 44 | 0.75 | 24 | 6 |
| 45 | 1.0 | 24 | 6 |
| 46 | 1.1 | 24 | 6 |
| 47 | 1.25 | 24 | 6 |
| 48 | 1.3 | 24 | 6 |
| 49 | 1.4 | 24 | 6 |
| 50 | 1.5 | 24 | 6 |

Each of the formulations listed in Table 1, further optionally contain an anesthetic and/or preservative. In some embodiments, the soluble and insoluble corticosteroids of each of the formulations disclosed in Table 1 can be replaced with corticosteroids selected from the group consisting of 1) methylprednisolone sodium succinate and methylprednisolone acetate; 2) prednisolone sodium succinate and prednisolone acetate; 3) triamcinolone acetonide phosphate ester and triamcinolone acetonide acetate; and 4) betamethasone sodium phosphate and betamethasone acetate.

Packaging and kits. The present formulation can be packaged in a unit dose vial or syringe. It can also be packaged in a two-compartment vial or syringe with the soluble and insoluble steroid each in a separate compartment. In some embodiments, the unit dose is between 1 mL and 10 mL; 2 mL and 8 mL; and 2 mL and 5 mL. In some embodiments, the unit dose is about 1 mL, about 2 mL, about 2.5 mL, about 3 mL, about 3.5 mL, about 4 mL, about 4.5 mL, about 5 mL, or about 5.5 mL. In any of the foregoing embodiments, the unit dose is a gel pharmaceutical composition. In other foregoing embodiments, the unit dose is an aqueous pharmaceutical composition. The present disclosure also provides for a kit comprising a pharmaceutical formulation disclosed herein and instructions for use.

In some of the foregoing embodiments, the pharmaceutical composition is aseptic. In some of the foregoing embodiments, the pharmaceutical composition is prepared using aseptic technique. For instance, the various components of the composition may be individually sterilized and then combined under aseptic conditions to provide the sterile pharmaceutical composition. In some of the foregoing embodiments, the pharmaceutical composition is terminally sterilized.

Methods

The present application also provides methods for treating inflammation and/or pain such as those associated with rheumatoid arthritis, osteoarthritis, lower back pain, tendonitis, spinal stenosis, disc herniation, radiculitis and chronic discogenic pain with any of the aqueous pharmaceutical compositions disclosed herein.

In one embodiment, the method comprises the steps of identifying an individual suffering from inflammation and/or pain, and injecting to the epidural space of the individual any of the aqueous pharmaceutical compositions disclosed herein. The method optionally comprises a step of injecting to the epidural space of the individual an anesthetic agent such as lidocaine, bupivacaine, or benzocaine. The anesthetic agent can be administered in a separate injection or can be combined with the aqueous pharmaceutical composition and injected together.

In another embodiment, the method comprises the steps of identifying an individual suffering from inflammation and/or pain, and injecting to a skin lesion of the individual any of the aqueous pharmaceutical compositions disclosed herein. The method optionally comprises a step of injecting to the skin lesion of the individual an anesthetic agent. The anesthetic agent can be administered in a separate injection or can be combined with the aqueous pharmaceutical composition and injected together.

In another embodiment, the method comprises the steps of identifying an individual suffering from inflammation and/or pain, and injecting to an affected joint of the individual any of the aqueous pharmaceutical compositions disclosed herein. The method optionally comprises a step of injecting to the affected joint of the individual an anesthetic agent. The anesthetic agent can be administered in a separate injection or can be combined with the pharmaceutical composition and injected together.

In some embodiments, the dose of the steroid injected is based on the potency of the steroid. In some embodiments, the amount of corticosteroid administered to an individual in a single dose is between 2 mg and 20 mg; 5 mg and 15 mg; and 5 mg and 10 mg. In some embodiments, the amount of corticosteroid administered to an individual in a single dose is about 2 mg, 5 mg, 8 mg, 10 mg, 15 mg and 20 mg.

In certain embodiments, the dosage of dexamethasone is about 3 to 20 mg/dose; the dosage of methylprednisolone is about 20 to 120 mg/dose, the dosage of prednisolone is about 20 to 120 mg/dose; the dosage of triamcinolone acetonide is about 20 to 120 mg/dose. The foregoing dosages represent the total amount of the insoluble and soluble corticosteroid in a dose.

In some embodiments, the individual is injected with the pharmaceutical composition once every 4 to 24 weeks; 6 to 20 weeks; or 8 to 12 weeks. In some embodiments, the individual is injected with the pharmaceutical composition about every 4, 6, 8, 12, 14, 16, 18, or 20 weeks.

The methods and compositions disclosed herein are useful in treating an individual that is a mammal, such as a human, dog or cat. The methods and compositions disclosed herein are particularly useful in treating humans.

Other Uses. Intralesional injection is a direct delivery of medication percutaneously into skin lesions. Intralesional injections are introduced into or performed within a lesion. The skin serves as a reservoir, allowing medication deposited in the dermis to be delivered over a period of time, resulting in prolonged therapy while avoiding or minimizing the adverse effects of systemic therapy.

Intra-articular injection is a procedure used in the treatment of inflammatory joint conditions, such as rheumatoid arthritis, psoriatic arthritis, gout, tendinitis, bursitis and occasionally osteoarthritis. A hypodermic needle is injected into the affected joint where it delivers an anti-inflammatory agent such as a corticosteroid.

The application discloses pharmaceutical compositions with a range of viscosities. The choice of the viscosity is in part dependent on the desired location of the injected pharmaceutical composition in the individual. For instance, when a localized amount of the pharmaceutical composition is desired, a pharmaceutical composition with a higher viscosity may be selected. Alternatively, if broader coverage of the pharmaceutical composition is desired, a pharmaceutical composition with a lower viscosity may be selected. In some embodiments, the method comprises administering the pharmaceutical composition via a transforaminal injection, wherein the pharmaceutical composition comprises between 0.75% and 1.5%, 1.0% and 1.5%, or 0.75% and 1.25%, of a viscosity enhancing agent. In some embodiments, the method comprises administering the pharmaceutical composition via an intralaminar injection, wherein the pharmaceutical composition comprises between 0.1% and 1.5%, 0.1% and 1.0%, 0.1% and 0.75%, 0.1% and 0.5%, 0.1% and 0.25%, 0.75% and 1.5%, 1.0% and 1.5%, or 0.75% and 1.25% of a viscosity enhancing agent. In some embodiments, the method comprises administering the pharmaceutical composition via a caudal injection, wherein the pharmaceutical composition comprises between 0.1% and 1.5%, 0.1% and 1.0%, 0.1% and 0.75%, 0.1% and 0.5%, or 0.1% and 0.25%, of a viscosity enhancing agent. In some of the foregoing embodiments, the viscosity enhancing agent is hyaluronic acid or a salt thereof.

Syringeability and injectability. Syringeability is the ability of an injectable therapeutic to pass easily through a hypodermic needle on transfer from a vial prior to an injection. Syringeability includes such factors as ease of withdrawal, clogging and foaming tendencies, and accuracy of dose measurements. Injectability refers to the performance of the formulation during injection. Injectability includes pressure or force required for injection, evenness of flow, and freedom from clogging (i.e., no blockage of the syringe needle). The syringability and injectability is influenced in part by the viscosity of the pharmaceutical composition, the injection or transfer flow rate, and the needle characteristics (such as length and gauge).

Desirable characteristics of injectability include, for example, a smooth and continuous injection without undue force. Such in injection allows the person administrating the injection to maintain continuous control over the procedure without incurring undue strain.

The application discloses compositions that are easily syringeable and/or injectable into an individual. The application also discloses methods for injecting an individual with a pharmaceutical composition, wherein the injecting is easy and provides a continuous flow of the pharmaceutical composition. In some embodiments, the method comprises applying an injecting force of between 5 N and 90 N, 5 N and 50 N, 50N and 100 N, 5 N and 25 N, 25 N and 50 N, or 10 N and 40 N to the syringe. In some embodiments, the method comprises applying a force of no more than 5 N, no more than 7 N, no more than 10 N, no more than 15 N, no more than 17, no more than 21 N, no more than 27 N, no more than 29 N, no more than 33 N, no more than 38 N, no more than 39 N, no more than 46 N, no more than 59 N, no more than 70, no more than 78 N or no more than 90 N to the syringe. In some embodiments, the method comprises applying a force of about 5 N, about 7 N, about 10 N, about 15 N, about 17, about 21 N, about 27 N, about 29 N, about 33 N, about 38 N, about 39 N, about 46 N, about 59 N, about 70, about 78 N or about 90 N to the syringe. In some embodiments, the injection force results in the injection of the pharmaceutical composition at a rate of about 0.4"/min, about 0.5"/min, about 0.6"/min, about 0.7"/min, about 0.8"/min, about 0.9"/min, about 1.0"/min, about 1.1"/min, about 1.2"/min, about 1.3"/min, about 1.4"/min, about 1.5"/min, about 1.75"/min, about 2.0"/min, about 2.25"/min, or at about 2.36"/min.

In any of the foregoing embodiments, the syringe comprises a needle having needle gauge of 19, 20, 21, 22, 23, 24, or 25.

The application discloses method for injection which reduces the "stringing effect". The stringing effect refers to a phenomenon that when the injection of the pharmaceutical composition into an individual is finished, the remaining composition in the bore of the needle used in the injection comes into contact with the individual. For instance, when the needle is withdrawn from the target site, the remaining composition in the bore of the needle is drawn out due to the viscous nature of the composition and elongates like string. The needle may leave a trail of the composition as it exits the individual, potentially exposing unintended areas and tissues to the composition. Unintended placement of the composition can lead to undesirable effects such as arachnoditis caused from an epidural injection. In some instances, upon withdrawal of the needle the composition injected into the target site may elongate and stretch and may come into contact with unintended areas and tissues of the individual.

In some embodiments, the methods and compositions disclosed herein reduce the occurrence of the stringing effect. In some embodiments, upon withdrawal from the injection site, no pharmaceutical composition disclosed herein exits the needle into the individual. In some embodiments, the pharmaceutical composition enters an individual only when an injection force is applied. In some embodiments, the composition makes a clean break with very little stringing upon separation or division.

In some embodiments, the application discloses a method for treating inflammation and/or pain in an individual in need thereof, comprising injecting an aqueous pharmaceutical composition disclosed herein into the epidural, intralesional, intra-articular or ocular space of the individual; and wherein the method comprises one or more of the steps selected from the group consisting of 1) applying a force of less than 5 N, less than 7 N, less than 10 N, less than 15 N, less than 17, or less than 21 N to inject the aqueous pharmaceutical composition at a rate of about 0.4"/min, about 0.5"/min, about 0.6"/min, about 0.7"/min, about 0.8"/min, about 0.9"/min, about 1.0"/min, about 1.1"/min, about 1.2"/min, about 1.3"/min, about 1.4"/min, about 1.5"/min, about 1.75"/min, about 2.0"/min, about 2.25"/min, or at about 2.36"/min.; and 2) injecting the aqueous pharmaceutical composition once every 4 to 24 weeks.

In some embodiments, the application discloses a method for treating inflammation and/or pain in an individual in need thereof, comprising injecting an aqueous pharmaceutical composition disclosed herein into the epidural, intralesional, intra-articular or ocular space of the individual; and wherein the method comprises one or more of the steps selected from the group consisting of 1) applying a force of less than 21 N to inject the aqueous pharmaceutical composition at a rate of about 0.5"/min; and 2) injecting the aqueous pharmaceutical composition once every 4 to 24 weeks.

In some embodiments, the application discloses a method for treating inflammation and/or pain in an individual in need thereof, comprising injecting any of the exemplary formulations in Table 1 into the epidural, intralesional, intra-articular or ocular space of the individual; and wherein the method comprises one or more of the steps selected from the group consisting of 1) applying a force of less than 5 N, less than 7 N, less than 10 N, less than 15 N, less than 17, or less than 21 N to inject the aqueous pharmaceutical composition at a rate of about 0.4"/min, about 0.5"/min, about 0.6"/min, about 0.7"/min, about 0.8"/min, about 0.9"/min, about 1.0"/min, about 1.1"/min, about 1.2"/min, about 1.3"/min, about 1.4"/min, about 1.5"/min, about 1.75"/min, about 2.0"/min, about 2.25"/min, or at about 2.36"/min.; and 2) injecting the aqueous pharmaceutical composition once every 4 to 24 weeks. In further embodiments, the step of injecting the aqueous pharmaceutical composition occurs about every 4, 6, 8, 12, 14, 16, 18, or 20 weeks.

In some embodiments, the application discloses a method for treating inflammation and/or pain in an individual in need thereof, comprising injecting any of the exemplary formulations in Table 1 into the epidural space of the individual; and wherein the method comprises one or more of the steps selected from the group consisting of 1) applying a force of less than 21 N to inject the aqueous pharmaceutical composition at a rate of about 0.5"/min; and 2) injecting the aqueous pharmaceutical composition once every 4 to 24 weeks. In further embodiments, the step of injecting the aqueous pharmaceutical composition occurs about every 4, 6, 8, 12, 14, 16, 18, or 20 weeks.

In some embodiments, the application discloses the use of an aqueous pharmaceutical composition, as described herein, in the manufacture of a formulation for the treatment of inflammation and/or pain in an individual in need thereof, wherein the formulation is injected into the individual.

The term "and/or" includes subject matter in the alternative as well as subject matter in combination. For instance, "x and/or y" includes "x or y" and "x and y".

The term "about" includes and describes the value or parameter per se. For example, "about x" includes and describes "x" per se. In certain embodiment, the term "about" when used in association with a measurement, or used to modify a value, a unit, a constant, or a range of values, refers to variations of +1-10%. In some embodiments, the term "about" when used in association with a measurement, or used to modify a value, a unit, a constant, or a range of values, refers to variations of +5%. In some embodiments, the term "about" when used in association with a measurement, or used to modify a value, a unit, a constant, or a range of values, refers to variations of +10%.

The term "between" includes and describes the value or parameter per se. For example, "between x and y" includes and describes "x" and "y" per se.

Any one of the foregoing embodiments may be combined with one or more other embodiments disclosed herein. For instance, by combining various embodiments disclosed herein a pharmaceutical composition comprising the ratio of 4:1 insoluble to soluble corticosteroid (embodiment a) of dexamethasone acetate/dexamethasone sodium phosphate combination (embodiment b), and sodium hyaluronate (embodiment c) in an amount of 0.05% w/v and 1.5% w/v (embodiment d) is provided by this application. In another instance, by combining various embodiments disclosed herein a method of treating inflammation and/or pain in an individual in need thereof (embodiment a) comprising injecting a pharmaceutical composition comprising the ratio of 4:1 insoluble to soluble corticosteroid (embodiment b) of dexamethasone acetate/dexamethasone sodium phosphate combination (embodiment c), and sodium hyaluronate (embodiment d) in an amount of 0.05% w/v and 1.5% w/v (embodiment e) is provided by this application.

The following examples further illustrate embodiments of the present application. These examples are intended merely to be illustrative of embodiments of the present application and are not to be construed as being limiting.

EXAMPLES

Example 1. Preparation of Dexamethasone Formulation Test Samples

This example describes test samples 1-3 used in the particle size, spreadability and dissolution studies detailed in Examples 2-4.

The molecular weight of the sodium hyaluronate used in test samples 1-3 is 1.56 MDa. 15 mM PBS (phosphate buffered saline) contained the following reagent concentrations: 2.75 mg/mL $Na_2HPO_4$-$7H_2O$; 0.65 mg/mL $NaH_2PO_4$—$H_2O$; 7.15 mg/mL NaCl. The total volume of the samples is 3 mL.

| | |
|---|---|
| Test Sample 1: | No sodium hyaluronate. 15 mM PBS, dexamethasone sodium phosphate (2 mg), dexamethasone acetate (8 mg). |
| Test Sample 2: | 1.0% w/v sodium hyaluronate, 15 mM PBS, dexamethasone sodium phosphate (2 mg), dexamethasone acetate (8 mg). |
| Test Sample 3: | 1.5% w/v sodium hyaluronate, 15 mM PBS, dexamethasone sodium phosphate (2 mg), dexamethasone acetate (8 mg). |

15 mM PBS was combined with sodium hyaluronate (1.0% w/v, molecular weight: 1.56 MDa), dexamethasone sodium phosphate (2 mg) and dexamethasone acetate (8 mg) to achieve a 3 mL volume. The mixture was stirred for several hours at room temperature to allow the sodium hyaluronate to hydrate. The resulting composition had a gel-like consistency and contained a suspension of dexamethasone acetate particles. Test sample 1 did not contain any sodium hyaluronate and test sample 3 was prepared in a similar fashion as test sample 2.

Example 2. Particle Size Analysis by Optical Microscopy

This example describes a particles size study of the dispersed phase by optical microscopy.

Test samples 1-3, described in Example 1, and samples of marketed product 1-3, described below, were evaluated by optical microscopy.

| | |
|---|---|
| Test Sample 1: | No sodium hyaluronate. 15 mM PBS, dexamethasone sodium phosphate (2 mg), dexamethasone acetate (8 mg). |
| Test Sample 2: | 1.0% w/v sodium hyaluronate, 15 mM PBS, dexamethasone sodium phosphate (2 mg), dexamethasone acetate (8 mg). |
| Test Sample 3: | 1.5% w/v sodium hyaluronate, 15 mM PBS, dexamethasone sodium phosphate (2 mg), dexamethasone acetate (8 mg). |
| Marketed Product 1: | Celestone Soluspan (Betamethasone sodium phosphate and betamethasone acetate Injectable Suspension, USP, 6 mg/mL, Merck/Lot#043753) |
| Marketed Product 2: | Depo-Medrol (Methylprednisolone acetate Injectable Suspension, USP, 40 mg/mL, Pfizer/Lot#H18976). |
| Marketed Product 3: | Kenalog-40 (Triamcinolone Acetonide Injectable Suspension, USP, 200 mg per 5 mL, BMS/Lot#3F75331). |

A drop of test sample or the marketed product samples were placed on a clean glass slide, and covered with a cover slip. The sample slide was transferred onto the microscopy stage, and observed at 40× magnification. A picture of representative microscopic field was taken. The size of 50 individual particles from the microscopic filed was measured using Image J computer program. Note: The particle size accuracy of the Image J computer program was verified using calibrated/standard Borosilicate Glass Microspheres with a nominal particle size of 10 microns. The average size, and the standard deviation of the 50 particles were calculated, and the particle size range was determined. A size distribution curve was generated using the particle size data. Any other observation such as agglomeration was also reported for each sample.

Particle size distribution in graphical format of test samples 1-3 and marketed products 1-3 are provided in FIGS. 1A-1F, respectively. Photomicrographs of the test samples and marketed products are shown in FIG. 2. Tables 2 and 3, below, provide details of the measurements for each of the particles of all the evaluated samples.

TABLE 2

Particle Size Analysis of Test Samples

| Particle number | Particle Size (microns) | | |
|---|---|---|---|
| | Test Sample#1 | Test Sample#2 | Test Sample#3 |
| 1 | 3.99 | 9.38 | 6.63 |
| 2 | 2.96 | 4.82 | 5.62 |
| 3 | 2.85 | 8.77 | 4.42 |
| 4 | 4.32 | 5.48 | 9.21 |
| 5 | 5.78 | 5.43 | 6.89 |
| 6 | 3.26 | 5.34 | 3.00 |
| 7 | 3.88 | 8.82 | 5.17 |
| 8 | 2.59 | 7.26 | 4.98 |
| 9 | 3.14 | 11.71 | 11.79 |
| 10 | 3.58 | 10.39 | 5.55 |
| 11 | 3.70 | 5.86 | 5.31 |
| 12 | 4.03 | 12.59 | 5.17 |
| 13 | 2.59 | 15.24 | 10.47 |
| 14 | 3.86 | 5.46 | 13.83 |
| 15 | 5.24 | 11.26 | 8.30 |
| 16 | 2.32 | 5.17 | 8.14 |
| 17 | 3.31 | 4.21 | 7.96 |
| 18 | 2.65 | 3.14 | 5.05 |
| 19 | 3.12 | 3.12 | 6.51 |
| 20 | 3.46 | 3.70 | 5.18 |
| 21 | 3.31 | 4.68 | 6.30 |
| 22 | 2.85 | 4.50 | 6.51 |
| 23 | 3.46 | 3.70 | 3.70 |
| 24 | 4.50 | 4.68 | 4.47 |
| 25 | 2.67 | 3.88 | 4.32 |
| 26 | 4.68 | 5.51 | 3.26 |
| 27 | 2.73 | 3.41 | 4.74 |
| 28 | 3.38 | 4.82 | 6.99 |
| 29 | 3.99 | 3.31 | 5.63 |
| 30 | 2.39 | 15.29 | 4.68 |
| 31 | 7.16 | 10.22 | 4.98 |
| 32 | 5.46 | 8.12 | 5.15 |
| 33 | 2.52 | 7.33 | 4.82 |
| 34 | 2.67 | 6.43 | 2.67 |
| 35 | 3.12 | 7.11 | 4.92 |
| 36 | 3.64 | 8.95 | 5.34 |
| 37 | 2.09 | 7.35 | 5.34 |
| 38 | 2.73 | 5.51 | 7.16 |
| 39 | 3.00 | 5.78 | 6.19 |
| 40 | 3.10 | 5.66 | 4.24 |
| 41 | 2.52 | 3.86 | 4.42 |
| 42 | 3.75 | 4.36 | 3.05 |
| 43 | 3.00 | 4.21 | 5.46 |
| 44 | 5.97 | 3.52 | 4.74 |
| 45 | 5.24 | 3.23 | 12.93 |
| 46 | 4.97 | 11.01 | 12.05 |
| 47 | 5.18 | 8.95 | 13.39 |
| 48 | 6.52 | 8.96 | 7.29 |
| 49 | 5.63 | 7.85 | 11.52 |
| 50 | 6.00 | 10.07 | 4.65 |
| Average size (microns) | 3.78 | 6.79 | 6.40 |
| SD | 1.23 | 3.11 | 2.78 |
| Size Range (microns) | 2.09 to 7.16 microns | 3.12 to 15.29 microns | 2.67 to 13.83 microns |
| Observations | Discrete particles; Uniform dispersion (Picture attached) | Few agglomerates (Picture attached) | Few agglomerates (Picture attached) |

TABLE 3

Particle Size Analysis of Marketed Samples

| Particle number | Particle Size (microns) | | |
|---|---|---|---|
| | Marketed Product 1 | Marketed Product 2 | Marketed Product 3 |
| 1 | 20.14 | 4.91 | 6.99 |
| 2 | 11.32 | 6.87 | 3.65 |
| 3 | 32.40 | 14.88 | 11.33 |
| 4 | 9.09 | 7.14 | 6.49 |
| 5 | 4.42 | 5.17 | 4.64 |
| 6 | 26.45 | 3.53 | 4.38 |
| 7 | 26.67 | 2.94 | 4.44 |
| 8 | 11.20 | 7.63 | 5.23 |
| 9 | 21.35 | 4.95 | 2.31 |
| 10 | 10.47 | 11.38 | 4.13 |
| 11 | 8.28 | 2.81 | 5.59 |
| 12 | 11.26 | 5.89 | 2.94 |
| 13 | 18.85 | 3.65 | 4.26 |
| 14 | 3.14 | 7.87 | 5.28 |
| 15 | 12.14 | 3.61 | 4.16 |
| 16 | 10.37 | 5.82 | 2.18 |
| 17 | 15.20 | 2.79 | 4.62 |
| 18 | 5.78 | 9.52 | 9.53 |
| 19 | 16.38 | 8.33 | 6.51 |
| 20 | 6.70 | 6.01 | 3.53 |
| 21 | 6.43 | 3.73 | 11.55 |
| 22 | 5.97 | 6.51 | 4.44 |
| 23 | 7.16 | 10.55 | 7.84 |
| 24 | 6.11 | 2.55 | 5.10 |
| 25 | 48.97 | 3.73 | 2.39 |
| 26 | 14.57 | 4.83 | 1.63 |
| 27 | 16.53 | 7.45 | 5.36 |
| 28 | 4.97 | 3.81 | 2.31 |
| 29 | 10.81 | 4.98 | 3.65 |
| 30 | 9.60 | 6.29 | 4.36 |
| 31 | 12.93 | 3.47 | 3.28 |
| 32 | 12.41 | 2.07 | 1.85 |
| 33 | 22.03 | 12.33 | 1.63 |
| 34 | 11.10 | 7.14 | 13.45 |
| 35 | 10.66 | 10.52 | 1.46 |
| 36 | 5.35 | 1.31 | 1.85 |
| 37 | 15.41 | 4.55 | 2.15 |
| 38 | 8.67 | 11.84 | 2.96 |
| 39 | 9.04 | 2.77 | 4.26 |
| 40 | 12.59 | 8.43 | 6.73 |
| 41 | 9.37 | 1.96 | 4.25 |
| 42 | 9.18 | 4.43 | 12.25 |
| 43 | 8.75 | 6.01 | 2.63 |
| 44 | 9.63 | 6.29 | 2.79 |
| 45 | 6.82 | 4.59 | 13.50 |
| 46 | 3.31 | 2.69 | 3.08 |
| 47 | 3.14 | 2.96 | 5.44 |
| 48 | 2.12 | 5.57 | 2.92 |
| 49 | 5.92 | 4.38 | 3.08 |
| 50 | 10.02 | 2.81 | 10.22 |
| Average size (microns) | 12.02 | 5.73 | 5.01 |
| SD | 8.34 | 3.01 | 3.14 |
| Size Range (microns) | 2.12 to 48.97 microns | 1.31 to 14.88 microns | 1.46 to 13.50 microns |
| Observations | Wide particle size distribution (Picture attached) | More agglomerates (Picture attached) | Few agglomerates (Picture attached) |

Example 3. Spreadability Testing

This example describes the spreadability study of test samples 1-3 using Webril Cotton Padding. Test samples 1-3 used in this study are described in Example 1.

| | |
|---|---|
| Test Sample 1: | No sodium hyaluronate. 15 mM PBS, dexamethasone sodium phosphate (2 mg), dexamethasone acetate (8 mg). |
| Test Sample 2: | 1.0% w/v sodium hyaluronate, 15 mM PBS, dexamethasone sodium phosphate (2 mg), dexamethasone acetate (8 mg). |
| Test Sample 3: | 1.5% w/v sodium hyaluronate, 15 mM PBS, dexamethasone sodium phosphate (2 mg), dexamethasone acetate (8 mg). |

Figure 3:
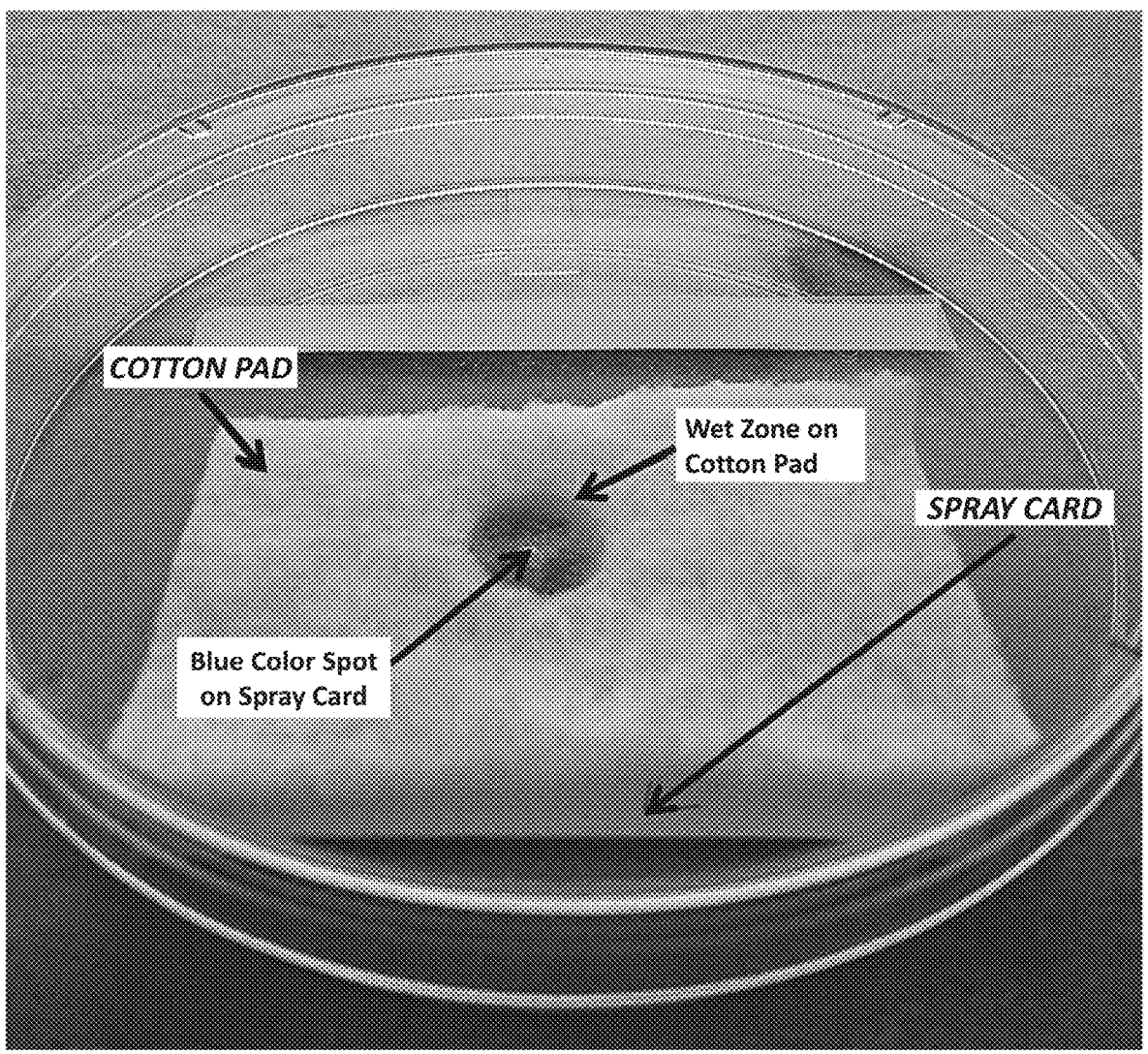
FIG. 3 shows a photograph of an exemplary setup for a spreadability test.
Figure 4:
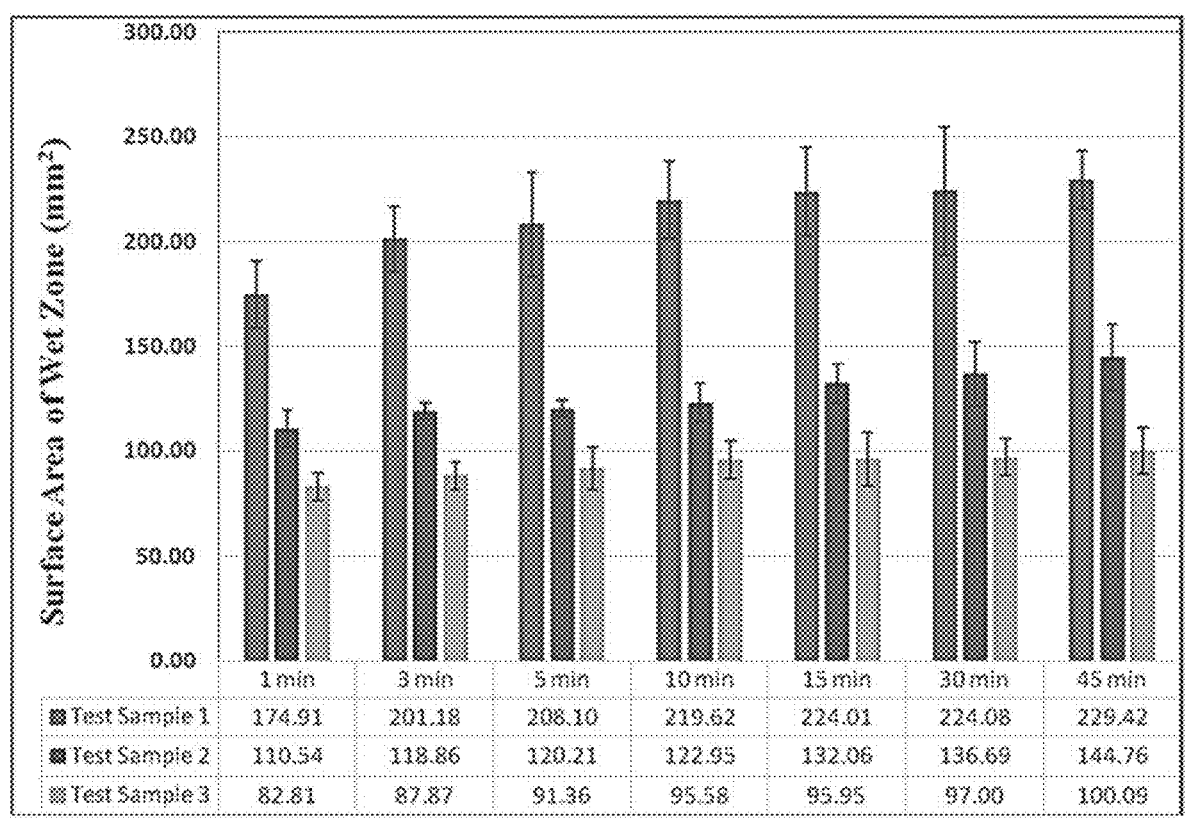
FIG. 4 summarizes spreadability results and the surface area of the wet zones on the cotton pad as a function of time for test samples 1-3.

Webril® Cotton Undercast Padding was cut from a roll into 52×38 mm dimension. The cotton padding was placed over a Teejet® water sensitive spray cards. The cotton padding along with the water sensitive card was placed in a closed petri plate, and labeled. A typical experimental set up is shown in FIG. 3. About 100 microliter of each sample was placed onto the cotton padding with the help of a syringe (without any needle attached) from minimal height. The dimensions of the wet zone on the cotton pad was measured using a digital caliper at 1, 3, 5, 10, 15, 30, and 45 minutes, and the surface area of wet zone at different time interval was calculated. The experiment was conducted in triplicate for each sample, under room temperature. The results are summarized in FIG. 4. At each time point, samples with a higher concentration of sodium hyaluronate had smaller wet zone surface areas. For instance, 45 minutes after applying the test samples to the cotton padding, the wet zones of test samples 1 (no sodium hyaluronate), 2 (1.0% w/v sodium hyaluronate), and 3 (1.5% w/v sodium hyaluronate) were 229 $mm^2$, 145 $mm^2$, and 100 $mm^2$, respectively.

Figure 5:
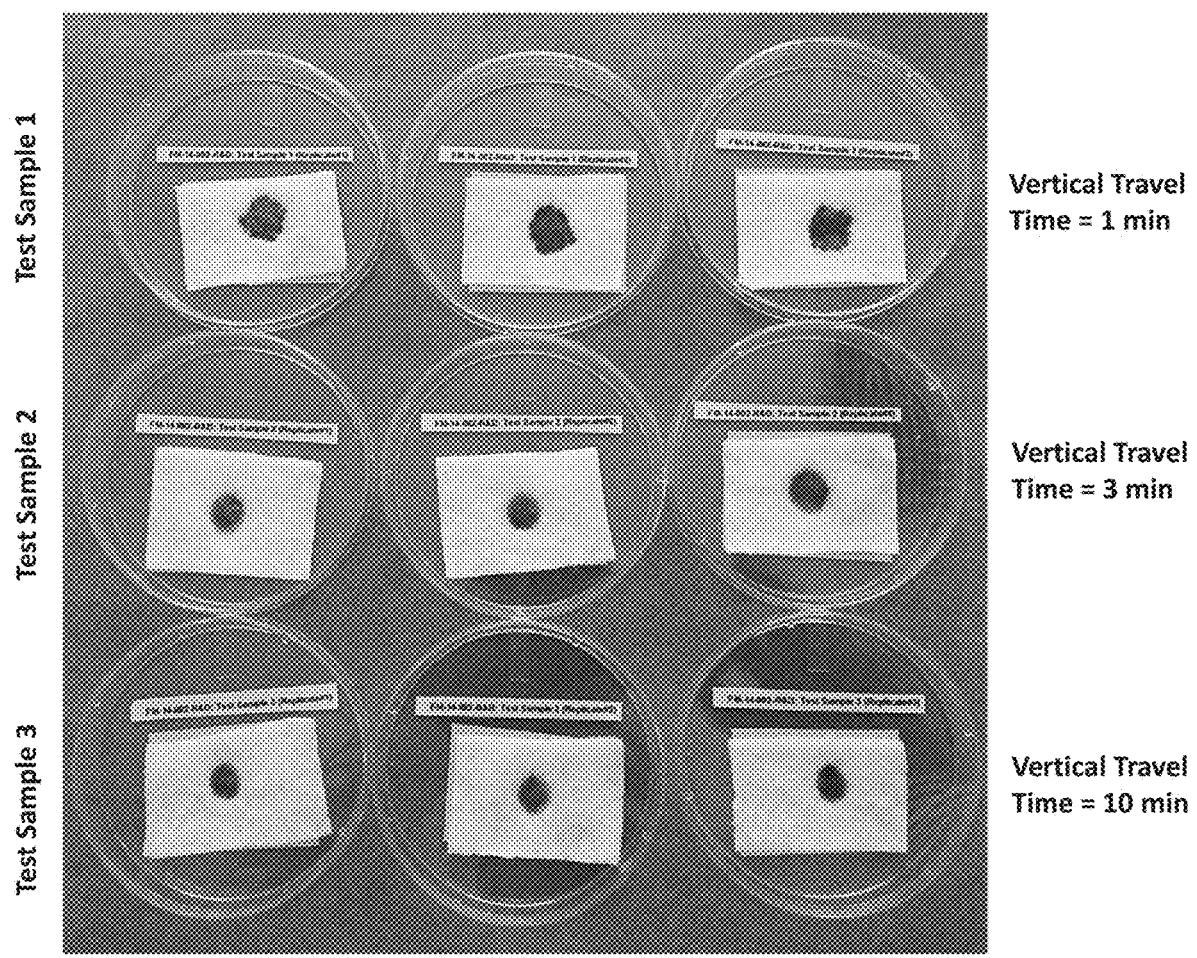
FIG. 5 shows a photograph of the three test samples in triplicate and summarizes the vertical travel time.

The length of time for the color change on the water sensitive spray card from yellow to blue was also noted. The time from application of the test sample to the appearance of blue color on the card represents the time taken by each sample to travel from the surface of the cotton pad to its bottom. The vertical travel time for test samples 1 (no sodium hyaluronate), 2 (1.0% w/v sodium hyaluronate), and 3 (1.5% w/v sodium hyaluronate) is 1 minute, 3 minute and 10 minutes, respectively. FIG. 5 shows a photograph of the three test samples in triplicate and summarizes the vertical travel time. This result suggests that the vertical travel time of the test samples increases with higher concentrations of sodium hyaluronate.

Example 4. In Vitro Dissolution Study of Dexamethasone

This Example describes in vitro dissolution testing for dexamethasone in test samples 1-3 using a USP Dissolution Apparatus. Test samples 1-3 used in this study are described in Example 1.

| | |
|---|---|
| Test Sample 1: | No sodium hyaluronate. 15 mM PBS, dexamethasone sodium phosphate (2 mg), dexamethasone acetate (8 mg). |
| Test Sample 2: | 1.0% w/v sodium hyaluronate, 15 mM PBS, dexamethasone sodium phosphate (2 mg), dexamethasone acetate (8 mg). |
| Test Sample 3: | 1.5% w/v sodium hyaluronate, 15 mM PBS, dexamethasone sodium phosphate (2 mg), dexamethasone acetate (8 mg). |

Figure 6:
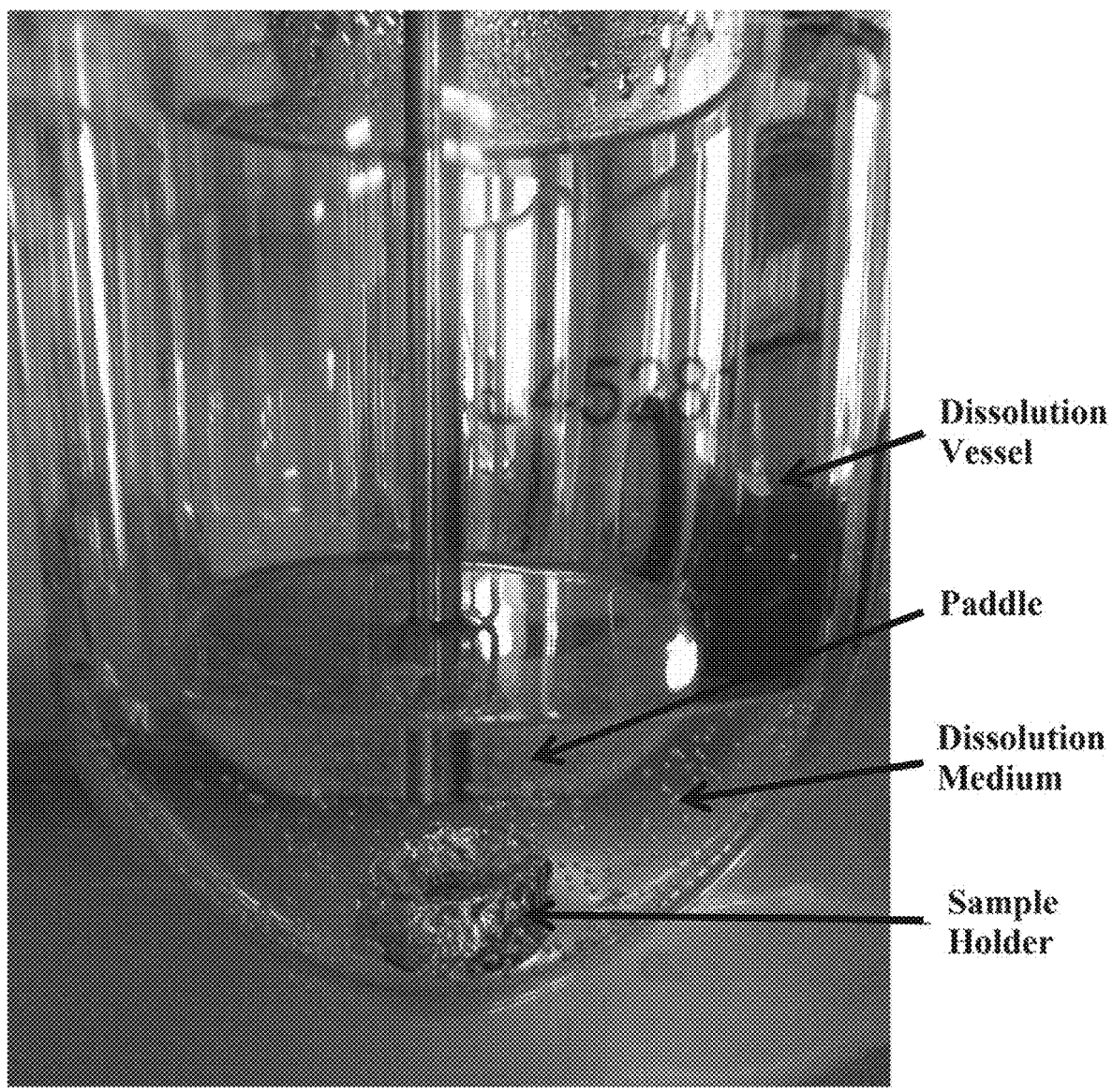
FIG. 6 shows a photograph of an exemplary setup for dissolution testing.
Figure 7A:
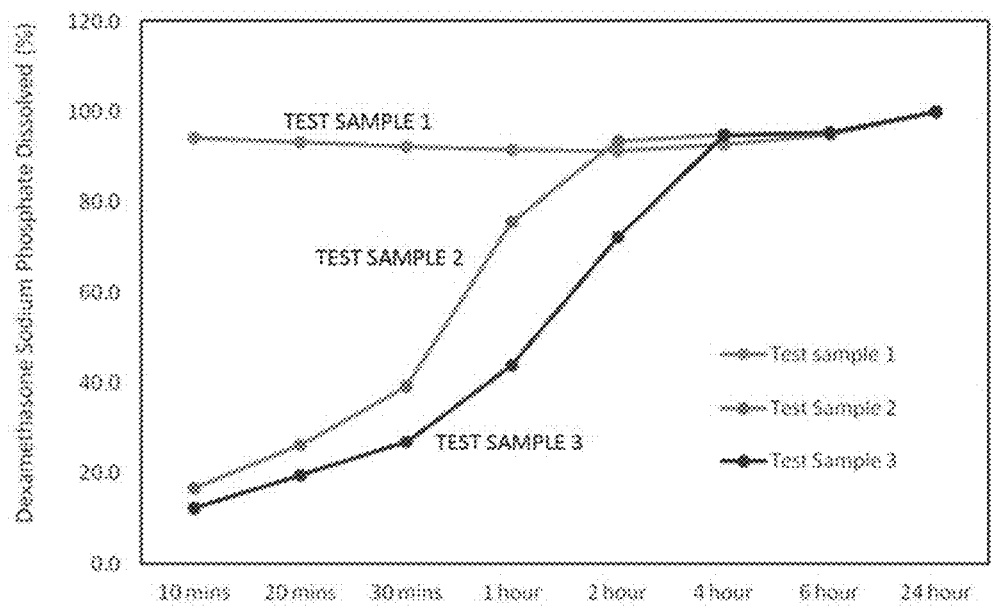
FIGS. 7A-7B shows a plot of the percentage of dexamethasone sodium phosphate (7A) and dexamethasone acetate (7B) dissolved as a function of time for each of test samples 1-3.
Figure 7B:
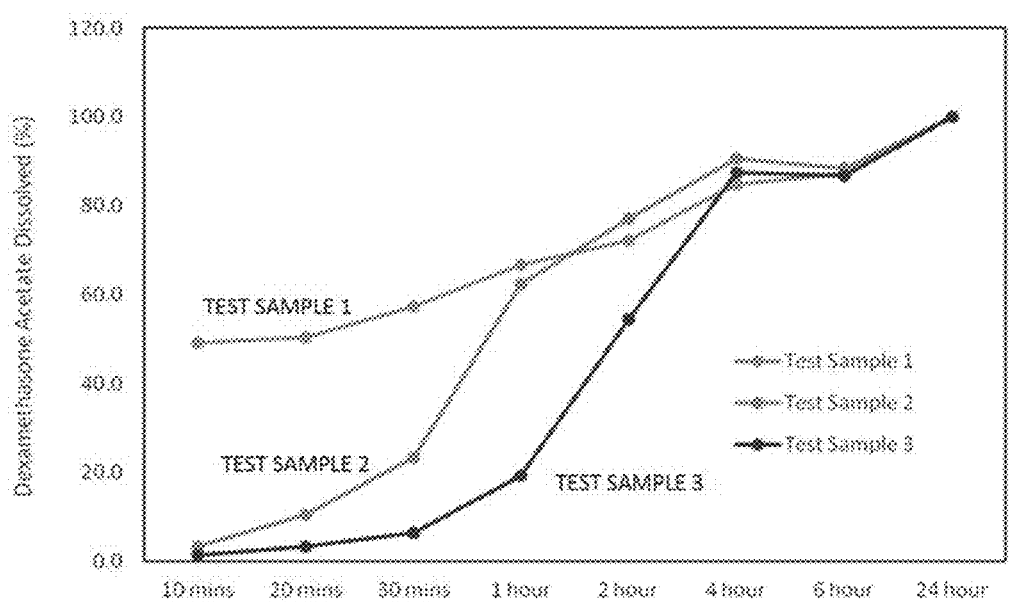

About 200 mL of purified water was transferred into dissolution vessels, and allowed to attain a temperature of 37° C. About 1 gram of test samples were transferred into sample holders, and placed into the bottom of the dissolution vessel. The study was conducted using Type 2 USP Dissolution Apparatus with paddle. A typical dissolution setup is shown in FIG. 6. The medium was stirred at 25 rpm, and 3 mL samples were withdrawn at 10 mins., 20 mins., 30 mins., 1 h, 2 h, 4 h, 6 h, and 24 h. After each sampling, 3 mL of purified water was replaced into the dissolution vessel. The samples were analyzed for the quantity of dexamethasone sodium phosphate and dexamethasone acetate by a HPLC method. Note: The above method was based on the assay method of dexamethasone sodium phosphate injection USP with modifications for the simultaneous estimation of dexamethasone sodium phosphate and dexamethasone acetate. Dissolution profile graphs for dexamethasone sodium phosphate and dexamethasone acetate were generated considering the amount of drug(s) dissolved at 24 hours is equivalent to 100% label claim. FIG. 7 shows a plot of the percentage of dexamethasone sodium phosphate (7A) and dexamethasone acetate (7B) dissolved as a function of time in each of the test samples 1-3.

Virtually all of the dexamethasone sodium phosphate in test sample 1, no sodium hyaluronate, is dissolved within the measurement at 10 minutes. At 1 hour, approximately 78% of the drug in test sample 2 (1.0% w/v of sodium hyaluronate) and approximately 42% of the drug in test sample 3 (1.5% w/v of sodium hyaluronate) is dissolved. At 2 hours, all of the drug in test sample 2 and approximately 72% of the drug in test sample 3 is dissolved.

Dissolution of dexamethasone acetate requires more time than the more soluble form of the drug. At 1 hour, approximately 68% of dexamethasone acetate is dissolved when no sodium hyaluronate is present in the formulation, test sample 1. At 1 hour, approximately 62% of the drug in test sample 2 (1.0% w/v of sodium hyaluronate) and approximately 20% of the drug in test sample 3 (1.5% w/v of sodium hyaluronate) is dissolved. At 2 hours, 78% of the drug in test sample 1, 72% of the drug in test sample 2 and approximately 54% of the drug in test sample 3 is dissolved.

These results suggest that increasing amounts of sodium hyaluronate result in a longer dissolution time of either dexamethasone sodium phosphate or dexamethasone acetate as.

Example 5. Formulations as a Function of Sodium Hyaluronate Molecular Weight and Concentration This example studies the effects of varying the molecular weight and concentration of sodium hyaluronate. It provides pH and Osmolality profiles and centrifugation observations and extrusion force measurements of the prepared formulations.

Formulations. 9 formulations were prepared using 15 mM PBS solution (3.11 mg/mL $Na_2HPO_4$-$7H_2O$; 0.47 mg/mL $NaH_2PO_4$—$H_2O$; and 6.7 mg/mL NaCl); 2 mg dexamethasone sodium phosphate; 8 mg dexamethasone acetate; and sodium hyaluronate. The total volume of each formulation was 3 mL. Each of the 9 formulations vary by the concentration and molecular weights of the sodium hyaluronate, as summarized in Tables 4-6. Three molecular weights of the viscosity enhancing agent were investigated: MW1 at 711 kDa, MW2 at 880 kDa and MW3 at 2,650 kDa. For each of the molecular weights, MW1-MW3, three different concentrations of sodium hyaluronate was used. The concentration as well as the measured pH and osmolality for each of the 9 formulations are summarized for MW1-MW3 in Tables 4-6.

TABLE 4

| NaHy MW | | MW1 711 kDa | |
| --- | --- | --- | --- |
| Concentration (%, w/w) | 2.0 | 3.0 | 4.0 |
| Target pH | | 7.3 ± 0.3 | |
| Actual pH | 7.5 | 7.5 | 7.5 |
| Target Osmolality (mOsm/kg) | | 285 ± 20 | |
| Actual Osmolality | 321 | 349 | 369 |

TABLE 5

| NaHy MW | | MW2 880 kDa | |
| --- | --- | --- | --- |
| Concentration (%, w/w) | 2.0 | 3.0 | 3.5 |
| Target pH | | 7.3 ± 0.3 | |
| Actual pH | 7.5 | 7.5 | 7.5 |
| Target Osmolality (mOsm/kg) | | 285 ± 20 | |
| Actual Osmolality | 324 | 348 | 360 |

TABLE 6

| NaHy MW | | MW3 2,650 kDa | |
| --- | --- | --- | --- |
| Concentration (%, w/w) | 1.5 | 2.0 | 2.5 |
| Target pH | | 7.3 ± 0.3 | |
| Actual pH | 7.5 | 7.5 | 7.5 |
| Target Osmolality (mOsm/kg) | | 285 ± 20 | |
| Actual Osmolality | 324 | 331 | 342 |

Centrifugation Observations. Each of the 9 sample formulations were placed in a test tube and centrifuged at 3500 rpm. Observations of the sample were made at 60 min and 90 min and are summarized in Table 7 below.

TABLE 7

| Sample | 60 min | 90 min |
| --- | --- | --- |
| MW1-20 mg/mL | Visible pellet settlement | Bigger pellet |
| MW1-30 mg/mL | Slightly visible pellet | Slightly bigger |
| MW1-40 mg/mL | No visible settlement | No visible settlement |
| MW2-20 mg/mL | Visible pellet settlement | Bigger pellet |
| MW2-30 mg/mL | No visible settlement | Slightly visible pellet |
| MW2-35 mg/mL | No visible settlement | No visible settlement |
| MW3-15 mg/mL | No visible settlement | No visible settlement |
| MW3-20 mg/mL | No visible settlement | No visible settlement |
| MW3-25 mg/mL | No visible settlement | No visible settlement |

Extrusion force measurements. The extrusion force required at two test speeds, 2.36"/minute and 0.5"/min, was measured for each of the 9 formulations described. The force measurements are summarized in Table 8. At each molecular weight, the amount of force required to achieve the test speeds increased as a function of increasing concentration of sodium hyaluronate.

TABLE 8

| | Test Speed | | | |
| --- | --- | --- | --- | --- |
| | 2.36"/minute | | 0.5"/minute | |
| Force | N | lbf | N | lbf |
| MW1-20 mg/mL | 37.5 | 8.4 | 27.7 | 6.2 |
| MW1-30 mg/mL | 70.0 | 15.8 | 58.1 | 13.1 |
| MW1-40 mg/mL | Did not perform test | | 97.3 | 21.9 |
| MW2-20 mg/mL | 39.4 | 8.9 | 29.8 | 6.7 |
| MW2-30 mg/mL | 69.6 | 15.7 | 59.2 | 13.3 |
| MW2-35 mg/mL | Exceeded max. force | | 78.0 | 17.5 |
| MW3-15 mg/mL | 20.6 | 4.6 | 17.3 | 3.9 |
| MW3-20 mg/mL | 32.9 | 7.4 | 27.2 | 6.1 |
| MW3-25 mg/mL | 46.2 | 10.4 | 39.7 | 8.9 |

Example 6. Formulations as a Function of 1.56 MDa Sodium Hyaluronate Concentration This example studies the effects of varying the concentration of sodium hyaluronate having a molecular weight of 1.56 MDa. It provides pH and Osmolality profiles and centrifugation observations and extrusion force measurements of the prepared formulations.

7 formulations were prepared using 15 mM PBS solution (2.75 mg/mL $Na_2HPO_4$-$7H_2O$; 0.65 mg/mL $NaH_2PO_4$—$H_2O$; 7.15 mg/mL NaCl); 2 mg dexamethasone sodium phosphate; 8 mg dexamethasone acetate; and sodium hyaluronate to achieve a 3 mL volume. The total volume of each formulation was 3 mL. Each of the 7 formulations varied by the concentration of the sodium hyaluronate (molecular weight 1.56 MDa). 7 concentrations of the viscosity enhancing agent were investigated: 0.1% w/v, 0.25% w/v, 0.5% w/v, 0.75% w/v, 1.0% w/v, 1.25% w/v and 1.5% w/v. The measured pH and osmolality for each of the 7 formulations are summarized in tables 9 and 10.

TABLE 9

| MW & Lot # | 1.56 MDa, Lot 024055 | | |
| --- | --- | --- | --- |
| Concentration (%, w/w) | 0.1 | 0.25 | 0.5 |
| Target pH | | 7.1 ± 0.3 | |
| Actual pH | 7.0 | 7.0 | 7.0 |
| Target Osmolality (mOsm/kg) | | 285 ± 20 | |
| Actual Osmolality | 266 | 269 | 273 |

TABLE 10

| MW & Lot # | 1.56 MDa, Lot 024055 | | | |
| --- | --- | --- | --- | --- |
| Concentration (%, w/w) | 0.75 | 1.0 | 1.25 | 1.5 |
| Target pH | | 7.1 ± 0.3 | | |
| Actual pH | 7.0 | 7.0 | 7.0 | 7.0 |
| Target Osmolality (mOsm/kg) | | 285 ± 20 | | |
| Actual Osmolality | 284 | 287 | 291 | 308 |

Figure 10:
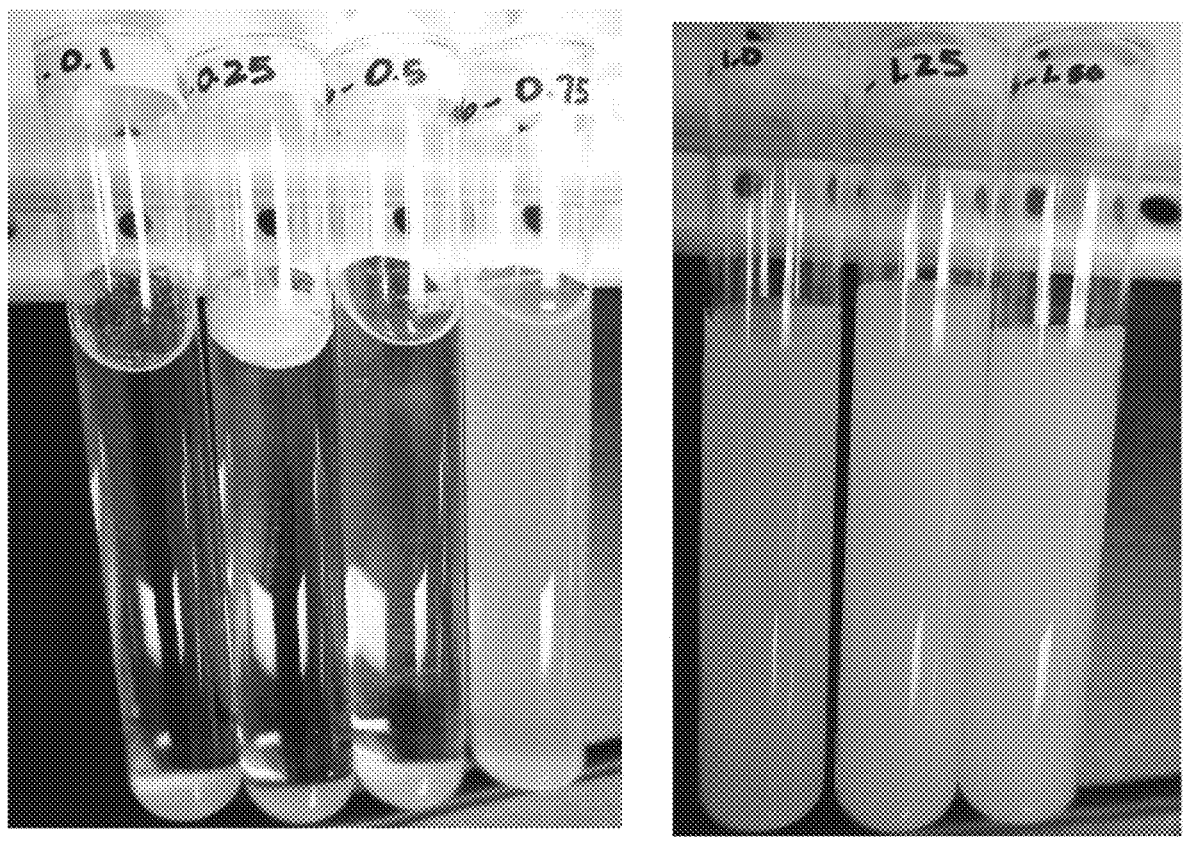
FIG. 10 shows photographs of formulations in a test tube that vary from 0.1% w/v to 1.50% w/v of sodium hyaluronate (1.56 MDa) after 90 minutes of centrifugation at 3500 rpm.
Figure 11:
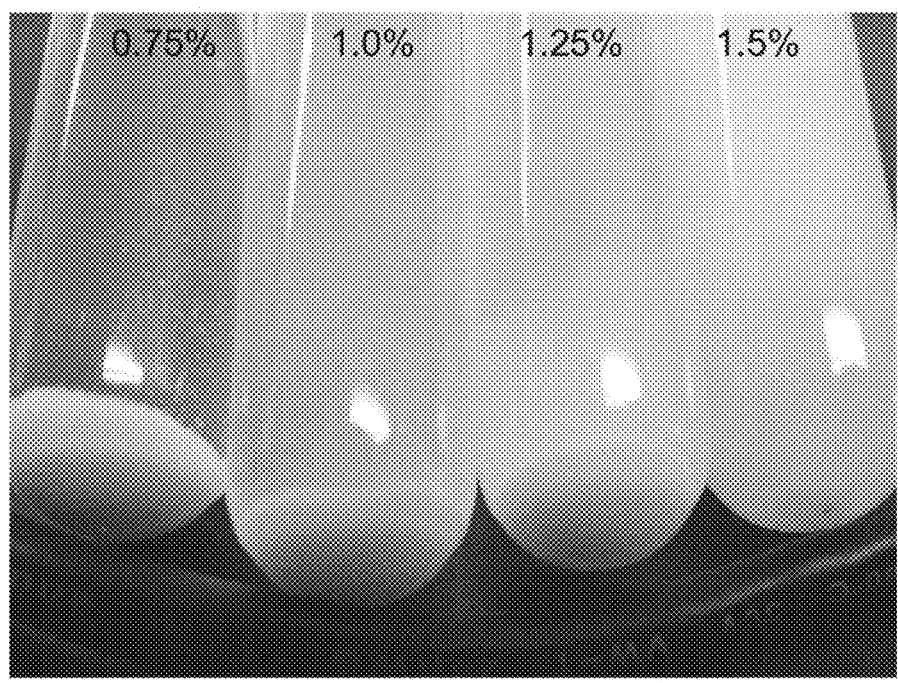
FIG. 11 shows an image of formulations in a test tube that vary from 0.75% w/v to 1.5% w/v of sodium hyaluronate (1.56 MDa) after 360 minutes of centrifugation at 3500 rpm.

Centrifugation Observations. Each of the 7 sample formulations were placed in a test tube and centrifuged at 3500 rpm at room temperature. Observations of the samples were made at 30 min., 90 min., 180 min., 270 min., and 360 min and are summarized in Table 11. Photographs of the test tubes were taken at 90 minutes and 360 minutes and are shown in FIGS. 10 and 11.

TABLE 11

| Sample | 30-min. | 90-min. | 180-min. | 270-min. | 360-min. |
|---|---|---|---|---|---|
| 0.1% | Complete separation w/big pellet | Complete separation w/big pellet | Complete separation w/big pellet | N/A | N/A |
| 0.25% | Complete separation w/big pellet | Complete separation w/big pellet | Complete separation w/big pellet | N/A | N/A |
| 0.5% | Some separation w/big pellet | Complete separation w/big pellet | Complete separation w/big pellet | N/A | N/A |
| 0.75% | Some separation, visible pellet | Some separation w/ visible pellet | Separation w/bigger pellet | Complete separation w/big pellet | Complete separation w/big pellet |
| 1.0% | Small pellet | Visible pellet | Bigger pellet | Bigger pellet | Big pellet |
| 1.25% | No pellet | No pellet | Slight pellet | Bigger pellet | Pellet |
| 1.5% | No pellet | No pellet | No pellet | Slight pellet | Visible pellet |

Extrusion force measurements. The extrusion force required at test speed 0.5"/min, was measured for each of the 7 formulations described. Increasing concentrations of sodium hyaluronate resulted in increasing amounts of extrusion force required to achieve the test speed. The force measurements are summarized in Table 12.

TABLE 12

| | Test Speed 0.5"/minute | |
|---|---|---|
| Concentration (%) | N | lbf |
| 0.10 | | |
| 0.25 | | |
| 0.50 | 4.93 | 1.1 |
| 0.75 | 7.28 | 1.6 |
| 1.00 | 10.27 | 2.3 |
| 1.25 | 15.33 | 3.4 |
| 1.50 | 20.87 | 4.7 |

Example 7. Calculated Estimates for Physical Properties of Formulations

Stoke's Law was used to calculate various physical properties as a function of particles size and viscosities.

$$V = gd^2(\rho_p - \rho_f)/18\eta \quad \text{Stoke's Law:}$$

V=Velocity in cm/s
g=gravitational acceleration in cm/s$^2$
d=diameter of spherical particle in cm
$\rho_p$=density of particle in g/cm$^3$
$\rho_f$=density of suspending media in g/cm$^3$
$\eta$=viscosity of suspending media in poises (g/cm-s)

Based on the parameters summarized below, the estimated minimum zero shear viscosity for particle sizes 8 μm and 5 μm to settle at a rate of less than or equal to 1 mm in 2 years is summarized below.

g (cm/s$^2$) = 980.665
$\rho_p$ (g/cm$^3$) ≈ 1.261
$\rho_f$ (g/cm$^3$) ≈ 1.01
d (μm) = 8
Estimated minimum zero shear viscosity to settle ≤ 1-mm in 2-year: ≥552 (kcP)

g (cm/s$^2$) = 980.665
$\rho_p$ (g/cm$^3$) ≈ 1.261
$\rho_f$ (g/cm$^3$) ≈ 1.01
d (μm) = 5
Estimated minimum zero shear viscosity to settle ≤ 1-mm in 2-year: ≥216 (kcP)

Three molecular weights of the viscosity enhancing agent were investigated: MW1 at 711 kDa, MW2 at 880 kDa and MW3 at 2,650 kDa. For each of the molecular weights, MW1-MW3, three different concentrations of sodium hyaluronate was used. The 9 formulations are summarized for MW1-MW3 in tables 4-6 of Example 5 and the predicted settling rates are summarized in Tables 13-15.

TABLE 13

Predicted number of days for 1 mm settle; Zero shear viscosity and estimated time for 8 μm particles.

| | MW | | | | | | | | |
|---|---|---|---|---|---|---|---|---|---|
| | MW1 711 kDa | | | MW2 880 kDa | | | MW3 2,650 kDa | | |
| mg/ml | 20 | 30 | 40 | 20 | 30 | 35 | 15 | 20 | 25 |
| η (kcP) | 25 | 98 | 253 | 49 | 202 | 348 | 769 | 2,420 | 5,502 |
| V (cm/s) | 3.6E−08 | 9.0E−09 | 3.4E−09 | 1.8E−08 | 4.3E−09 | 2.5E−09 | 1.1E−09 | 3.6E−10 | 1.6E−10 |
| Days for 1-mm Settle | 33 | 129 | 335 | 64 | 268 | 461 | 1017 | 3200 | 7276 |

TABLE 14

Predicted number of days for 1 mm settle; Viscosity @ 0.3/s and estimated time for 8 μm particles.

| | MW | | | | | | | | |
|---|---|---|---|---|---|---|---|---|---|
| | MW1 711 kDa | | | MW2 880 kDa | | | MW3 2,650 kDa | | |
| mg/ml | 20 | 30 | 40 | 20 | 30 | 35 | 15 | 20 | 25 |
| η (kcP) | 16 | 77 | 209 | 39 | 159 | 269 | 205 | 426 | 652 |

TABLE 14-continued

Predicted number of days for 1 mm settle; Viscosity @ 0.3/s and estimated time for 8 μm particles.

| | MW | | | | | | | | |
|---|---|---|---|---|---|---|---|---|---|
| | MW1 711 kDa | | | MW2 880 kDa | | | MW3 2,650 kDa | | |
| V (cm/s) | 5.3E−08 | 1.1E−08 | 4.2E−09 | 2.2E−08 | 5.5E−09 | 3.2E−09 | 4.3E−09 | 2.1E−09 | 1.3E−09 |
| Days for 1-mm Settle | 22 | 102 | 276 | 52 | 211 | 356 | 271 | 563 | 862 |

TABLE 15

Predicted number of days for 1 mm settle; viscosity @ 1/s and estimated time for 8 μm particles.

| | MW | | | | | | | | |
|---|---|---|---|---|---|---|---|---|---|
| | MW1 711 kDa | | | MW2 880 kDa | | | MW3 2,650 kDa | | |
| mg/ml | 20 | 30 | 40 | 20 | 30 | 35 | 15 | 20 | 25 |
| η (kcP) | 15 | 67 | 171 | 33 | 124 | 194 | 99 | 196 | 295 |
| V (cm/s) | 5.8E−08 | 1.3E−08 | 5.1E−09 | 2.6E−08 | 7.1E−09 | 4.5E−09 | 8.9E−09 | 4.5E−09 | 3.0E−09 |
| Days for 1-mm Settle | 20 | 88 | 226 | 44 | 163 | 257 | 131 | 260 | 390 |

Figure 8:
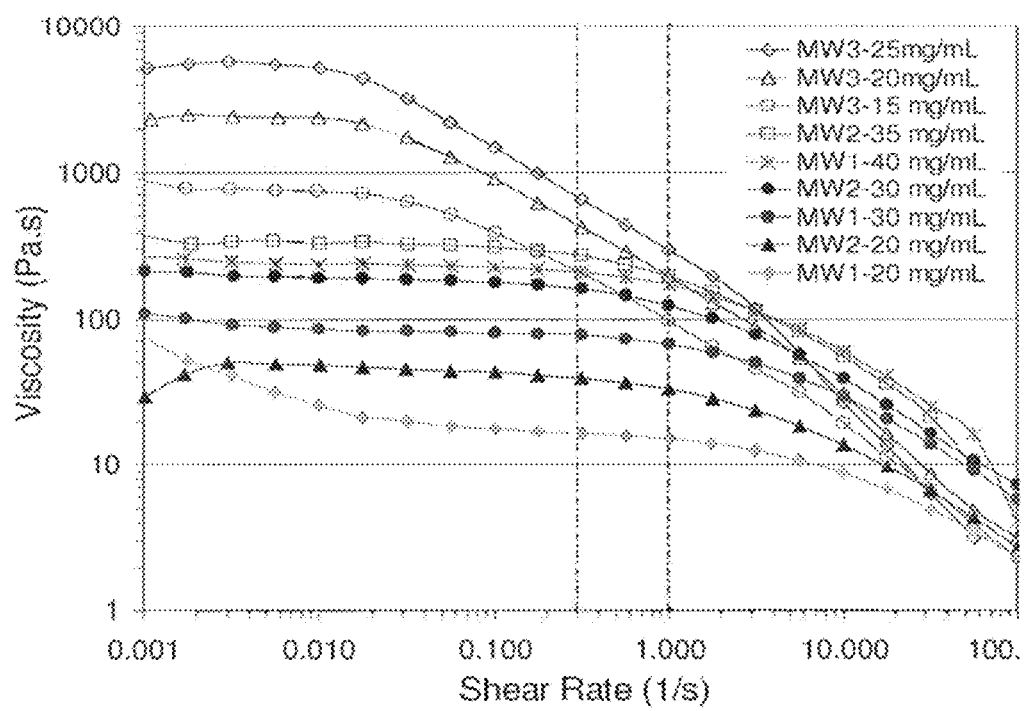
FIG. 8 shows the relationship between viscosity and shear force for various formulations that vary by sodium hyaluronate molecular weight and concentration.

FIG. 8 shows the relationship between viscosity and shear force as calculated for the various samples. The results show that as increasing shear is applied to the sample, the measured viscosity decreases, and suggests that high viscosity samples are relatively easy to inject.

Example 8. Calculated Estimates for Physical Properties of Formulations

Stoke's Law was used to calculate various physical properties.

Based on the parameters summarized below, the estimated minimum zero shear viscosity for particle sizes 8 μm and 5 nm to settle at a rate of less than or equal to 1 mm in 2 years is summarized below.

$g\ (cm/s^2) = 980.665$
$\rho_p\ (g/cm^3) \approx 1.261$ (Crystal Steroid)
$\rho_f\ (g/cm^3) \approx 1.01$
$d\ (\mu m) = 8$ (Crystal Steroid)
Estimated minimum zero shear viscosity to settle ≤ 1-mm in 2-year: ≥552 (kcP)

$g\ (cm/s^2) = 980.665$
$\rho_p\ (g/cm^3) \approx 1.299$ (Sanofi Steroid)
$\rho_f\ (g/cm^3) \approx 1.01$
$d\ (\mu m) = 5$ (Sanofi Steroid)
Estimated minimum zero shear viscosity to settle ≤ 1-mm in 2-year: ≥248 (kcP)

Varying concentration of sodium hyaluronate having a molecular weight of 1.56 MDa was investigated. 7 concentrations of the viscosity enhancing agent were investigated: 0.1% w/v, 0.25% w/v, 0.5% w/v, 0.75% w/v, 1.0% w/v, 1.25% w/v and 1.5% w/v. The 7 formulations are summarized in tables 9 and 10 and described in Example 6, and the predicted settling rates are summarized in tables 16-22.

TABLE 16

Predicted number of days for 1 mm settle; Zero shear viscosity and estimated time for 5 μm particles at 25° C.

| | 1.56 MDa, Lot 024055 | | | | | | |
|---|---|---|---|---|---|---|---|
| NaHy (%) | 0.1 | 0.25 | 0.5 | 0.75 | 1.0 | 1.25 | 1.5 |
| η (kcP) | Not Tested | 6 | 18 | 24 | 81 | 158 | |
| V (cm/s) | | 6.4E−08 | 2.2E−08 | 1.6E−08 | 4.9E−09 | 2.5E−09 | |
| Days for 1-mm Settle | | 18 | 53 | 71 | 238 | 464 | |

TABLE 17

Predicted number of days for 1 mm settle; Zero shear viscosity and estimated time for 5 μm particles at 5° C.

| | 1.56 MDa, Lot 024055 | | | |
|---|---|---|---|---|
| NaHy (%) | 0.75 | 1.0 | 1.25* | 1.5 |
| η (kcP) | 40 | 70 | 116* | 388 |
| V (cm/s) | 9.83E−09 | 5.66E−09 | 3.39E−09 | 1.01E−09 |

TABLE 17-continued

Predicted number of days for 1 mm settle; Zero shear viscosity and estimated time for 5 μm particles at 5° C.

| | 1.56 MDa, Lot 024055 | | | |
|---|---|---|---|---|
| NaHy (%) | 0.75 | 1.0 | 1.25* | 1.5 |
| Days for 1-mm Settle | 118 | 205 | 341* | 1141 |

*The re-test results at 25° C. indicated that 1.25% sample had viscosity decrease, but others did not.

TABLE 18

Predicted number of days for 1 mm settle; Zero Shear Viscosity and temperature for 5 μm particles, varying sodium hyaluronate concentration from 0.75% w/v to 1.50% w/v.

| | | 0.75% | 1.00% | 1.25% | 1.50% |
|---|---|---|---|---|---|
| 25° C. | η (cP) | 18,060 | 24,065 | 81,047 | 157,900 |
| | Days for 1 mm settle | 53 | 71 | 238 | 464 |
| 5° C. | η (cP) | 40,060 | 69,555 | 116,133 | 388,100 |
| | Days for 1 mm settle | 118 | 205 | 341* | 1141 |

*The re-test results at 25° C. indicated that 1.25% sample had viscosity decrease, but others did not.

TABLE 19

Predicted number of days for 1 mm settle; Viscosity @ 0.3/s and estimated time for 5 μm particles at 25° C., varying sodium hyaluronate concentration from 0.1% w/v to 1.50% w/v.

| | 1.56 MDa, Lot 024055 | | | | | | |
|---|---|---|---|---|---|---|---|
| NaHy (%) | 0.1 | 0.25 | 0.5 | 0.75 | 1.0 | 1.25 | 1.5 |
| η (kcP) | Not Tested | | 1 | 7 | 21 | 49 | 90 |
| V (cm/s) | | | 3.2E−07 | 5.5E−08 | 1.8E−08 | 8.1E−09 | 4.4E−09 |
| Days for 1-mm Settle | | | 4 | 21 | 63 | 143 | 266 |

TABLE 20

Predicted number of days for 1 mm settle; Viscosity @ 0.3/s and estimated time for 5 μm particles at 5° C., varying sodium hyaluronate concentration from 0.1% w/v to 1.50% w/v.

| | 1.56 MDa, Lot 024055 | | | |
|---|---|---|---|---|
| NaHy (%) | 0.75 | 1.0 | 1.25* | 1.5 |
| η (kcP) | 16 | 45 | 62* | 181 |
| V (cm/s) | 2.40E−08 | 8.75E−09 | 6.32E−09 | 2.17E−09 |
| Days for 1-mm Settle | 48 | 132 | 183* | 532 |

*The re-test results at 25° C. indicated that 1.25% sample had viscosity decrease, but others did not.

TABLE 21

Predicted number of days for 1 mm settle; Viscosity @ 1/s and estimated time for 5 μm particles at 25° C., varying sodium hyaluronate concentration from 0.1% w/v to 1.50% w/v.

| | 1.56 MDa, Lot 024055 | | | | | | |
|---|---|---|---|---|---|---|---|
| NaHy (%) | 0.1 | 0.25 | 0.5 | 0.75 | 1.0 | 1.25 | 1.5 |
| η (kcP) | Not Tested | | 1 | 6 | 16 | 33 | 57 |
| V (cm/s) | | | 3.4E−07 | 6.9E−08 | 2.5E−08 | 1.2E−08 | 6.9E−09 |
| Days for 1-mm Settle | | | 3 | 17 | 47 | 97 | 168 |

TABLE 22

Predicted number of days for 1 mm settle; Viscosity @ 1/s and estimated time for 5 μm particles at 5° C., varying sodium hyaluronate concentration from 0.75% w/v to 1.50% w/v.

| | 1.56 MDa, Lot 024055 | | | |
|---|---|---|---|---|
| NaHy (%) | 0.75 | 1.0 | 1.25* | 1.5 |
| η (kcP) | 12 | 29 | 40* | 98 |
| V (cm/s) | 3.38E−08 | 1.38E−08 | 9.96E−09 | 4.01E−09 |
| Days for 1-mm Settle | 34 | 84 | 116* | 289 |

*The re-test results at 25° C. indicated that 1.25% sample had viscosity decrease, but others did not.

Figure 9:
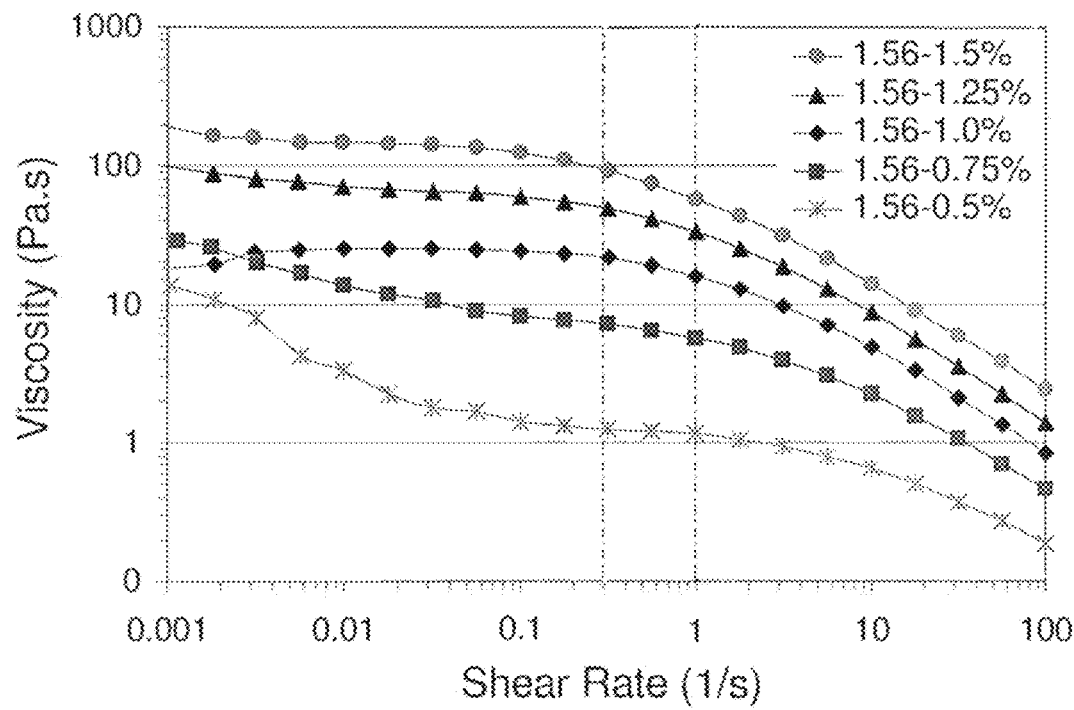
FIG. 9 shows the relationship between viscosity and shear force for various formulations that vary by sodium hyaluronate concentration (MW 1.56 MDa).

FIG. 9 shows the relationship between viscosity and shear force as calculated for various formulations as a function of sodium hyaluronate concentration (MW 1.56 MDa). The results show that as increasing shear is applied to the sample, the measured viscosity decreases, and suggests that high viscosity samples are relatively easy to inject.

What is claimed is:

1. A syringe comprising an aqueous pharmaceutical composition, wherein the aqueous pharmaceutical composition comprises:
   an insoluble corticosteroid, a soluble corticosteroid, and at least one viscosity enhancing agent;
   wherein the at least one viscosity enhancing agent is sodium hyaluronate or hyaluronic acid, and the soluble corticosteroid is dexamethasone sodium phosphate and the insoluble corticosteroid is dexamethasone acetate,
   wherein the molecular weight of the at least one viscosity enhancing agent is between 1.0 MDa and 2.5 MDa; and
   wherein the concentration of the at least one viscosity enhancing agent is between 1.0% w/v and 1.5% w/v.

2. A syringe comprising an aqueous pharmaceutical composition, wherein the aqueous pharmaceutical composition comprises:
   an insoluble corticosteroid, a soluble corticosteroid, and at least one viscosity enhancing agent;
   wherein the at least one viscosity enhancing agent is sodium hyaluronate or hyaluronic acid, and the insoluble corticosteroid and soluble corticosteroid are selected from the group consisting of salts and esters of methylprednisolone,
   wherein the molecular weight of the at least one viscosity enhancing agent is between 1.0 MDa and 2.5 MDa; and
   wherein the concentration of the at least one viscosity enhancing agent is between 1.0% w/v and 1.5% w/v.

3. The syringe of claim 1, wherein the at least one viscosity enhancing agent is sodium hyaluronate.

4. The syringe of claim 1, wherein the at least one viscosity enhancing agent is hyaluronic acid.

5. The syringe of claim 1, wherein the weight ratio or molar ratio of soluble corticosteroid to insoluble corticosteroid ranges from about 1:4 to about 4:1.

6. The syringe of claim 1, wherein the weight ratio or molar ratio of soluble corticosteroid to insoluble corticosteroid is 1:4.

7. The syringe of claim 1, wherein the molecular weight of the at least one viscosity enhancing agent is between 1.2 MDa and 1.8 MDa.

8. The syringe of claim 1, wherein the molecular weight of the at least one viscosity enhancing agent is about 1.56 MDa.

9. The syringe of claim 1, wherein the concentration of the at least one viscosity enhancing agent is about 1.25% w/v.

10. The syringe of claim 1, wherein the at least one viscosity enhancing agent is sodium hyaluronate,
    wherein the molecular weight of the sodium hyaluronate is between 1.0 MDa and 2.0 MDa, and the concentration of the sodium hyaluronate is about 1.25% w/v.

11. The syringe of claim 1, wherein the dexamethasone sodium phosphate and the dexamethasone acetate are present at a weight equivalent to achieve a dexamethasone concentration of about 5 mg/mL.

12. A method for treating inflammation and/or pain in an individual in need thereof, comprising injecting an aqueous pharmaceutical composition into the individual in need thereof;
    wherein the aqueous pharmaceutical composition is administered by ft the syringe of claim 1.

13. The method of claim 12, wherein the aqueous pharmaceutical composition is injected into an intralesional or intra-articular space.

14. The method of claim 12, wherein less than 20 N of force is used to inject the aqueous pharmaceutical composition.

15. The method of claim 12, wherein the individual in need thereof is injected with the aqueous pharmaceutical composition once every 4 to 24 weeks.

16. The method of claim 12, wherein the at least one viscosity enhancing agent is sodium hyaluronate,
    wherein the molecular weight of the sodium hyaluronate is between 1.0 MDa and 2.0 MDa, and the concentration of the sodium hyaluronate is about 1.25% w/v.

17. The method of claim 12, wherein dexamethasone sodium phosphate and dexamethasone acetate are present at a weight equivalent to achieve a dexamethasone concentration of about 5 mg/mL.

18. The method of claim 12, wherein the at least one viscosity enhancing agent is sodium hyaluronate.

19. The method of claim 12, wherein the at least one viscosity enhancing agent is hyaluronic acid.

20. The method of claim 12, wherein the concentration of the at least one viscosity enhancing agent is about 1.25% w/v.

* * * * *

UNITED STATES PATENT AND TRADEMARK OFFICE
CERTIFICATE OF CORRECTION

PATENT NO. : 11,364,251 B2
APPLICATION NO. : 16/921628
DATED : June 21, 2022
INVENTOR(S) : Mahendra G. Shah Page 1 of 1

It is certified that error appears in the above-identified patent and that said Letters Patent is hereby corrected as shown below:

In the Claims

At Column 30, Claim number 12, Line number 27:
"administered by ft the syringe" should read -- administered by the syringe --

Signed and Sealed this
Twenty-seventh Day of September, 2022

Katherine Kelly Vidal
*Director of the United States Patent and Trademark Office*